(12) United States Patent
Pourmand

(10) Patent No.: US 12,196,750 B2
(45) Date of Patent: Jan. 14, 2025

US012196750B2

(54) METHODS FOR SIMULTANEOUS DETECTION OF ANALYTES AND APPARATUSES FOR PRACTICING SAME

(71) Applicant: The Regents of the University of California, Oakland, CA (US)

(72) Inventor: Nader Pourmand, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 1191 days.

(21) Appl. No.: 16/969,146

(22) PCT Filed: Feb. 11, 2019

(86) PCT No.: PCT/US2019/017475
§ 371 (c)(1),
(2) Date: Aug. 11, 2020

(87) PCT Pub. No.: WO2019/157434
PCT Pub. Date: Aug. 15, 2019

(65) Prior Publication Data
US 2021/0041426 A1  Feb. 11, 2021

Related U.S. Application Data

(60) Provisional application No. 62/629,547, filed on Feb. 12, 2018.

(51) Int. Cl.
*G01N 33/543* (2006.01)
*B01L 3/02* (2006.01)
*G01N 27/48* (2006.01)

(52) U.S. Cl.
CPC .......... *G01N 33/5438* (2013.01); *B01L 3/021* (2013.01); *G01N 27/48* (2013.01); *B01L 2300/0645* (2013.01); *G01N 2333/4703* (2013.01); *G01N 2440/14* (2013.01)

(58) Field of Classification Search
None
See application file for complete search history.

(56) References Cited

U.S. PATENT DOCUMENTS

| | | | | |
|---|---|---|---|---|
| 9,267,919 | B1* | 2/2016 | Larkins | G01N 33/48707 |
| 2010/0072080 | A1* | 3/2010 | Karhanek | G01N 27/4035 |
| | | | | 205/792 |
| 2012/0222958 | A1* | 9/2012 | Pourmand | G01N 27/3277 |
| | | | | 977/700 |
| 2012/0225435 | A1* | 9/2012 | Seger | B01L 3/502715 |
| | | | | 435/7.1 |

FOREIGN PATENT DOCUMENTS

| FR | 2692357 | * | 6/1992 | ........... G01N 33/532 |
|---|---|---|---|---|
| WO | WO 2014160036 | * | 2/2014 | ............ G01N 33/53 |
| WO | WO 2016138116 | * | 9/2016 | ............ G01N 27/49 |

OTHER PUBLICATIONS

Nascimento et al. (2016) "Single cell "Glucose Nanosensor" Verifies Elevated Glucose Levels in Individual Cancer Cells" Nano Lett. 161194-1200.*
Umehara (2009) "Label-free biosensing with functionalized nanopipette probes" PNAS 106(12): 4611-4616.*
Actis et al. (2010) "Functionalized nanopipettes: toward label-free, single cell biosensors" Bioanal. Rev. 1:177-185.
Actis et al. (2011) "Reversible thrombin detection by aptamer functionalized STING sensors" Biosens. Bioelectron. 26:4503-4507.
Actis et al. (2012) "Copper Sensing with a Prion Protein Modified Nanopipette" 2(31):11638-11640.
Actis et al. (2014) "Compartmental Genomics in Living Cells Revealed by Single-Cell Nanobiopsy" ACS Nano. 8:546-553.
Alizadeh et al. (2017) "A highly sensitive electrochemical immunosensor for hepatitis B virus surface antigen detection based on Hemin/Gquadruplex horseradish peroxidase-mimicking DNAzyme-signal amplification" Biosens. Bioelectron. 94:184-192.
Andl et al. (2004) "EGFR-induced cell migration is mediated predominantly by the JAK-STAT pathway in primary esophageal keratinocytes" Am. J. Physiol.—Gastrointest. Liver Physiol. 287:G1227-G1237.
Battaglia et al. (2013) "Interleukin-21 (IL-21) synergizes with IL-2 to enhance T-cell receptor-induced human T-cell proliferation and counteracts IL-2/transforming growth factor-B-induced regulatory T-cell development" Immunology. 139:109-120.
Bodenmiller et al. (2012) "Multiplexed mass cytometry profiling of cellular states perturbed by small-molecule regulators" Nat. Biotechnol. 30:858-867.
Boersema et al. (2010) "In-depth qualitative and quantitative profiling of tyrosine phosphorylation using a combination of phosphopeptide immunoaffinity purification and stable isotope dimethyl labeling" Mol. Cell. Proteomics MCP 9:84-99.
Croce et al. (2015) "IL-21: A Pleiotropic Cytokine with Potential Applications in Oncology" Journal of Immunology Research. Article ID 696578, 15 pages. doi:10.1155/2015/696578.
Dien Bard et al. (2009) "IL-21 Contributes to JAK3/STAT3 Activation and Promotes Cell Growth in ALK-Positive Anaplastic Large Cell Lymphoma" Am. J. Pathol. 175:825-834.

(Continued)

*Primary Examiner* — Ann Montgomery
(74) *Attorney, Agent, or Firm* — Brian E. Davy; Bozicevic, Field & Francis LLP

(57) ABSTRACT

Provided are methods for simultaneously detecting analytes. The methods include exposing a tip of a nanosensor to a biological sample, measuring ionic current flow through the nanosensor tip to detect a first analyte and a second analyte in the biological sample, and distinguishing the first analyte from the second analyte based on a first diffusion limited current peak resulting from binding of a first specific binding member to the first analyte being distinguishable from a second diffusion limited current peak resulting from binding of a second specific binding member to the second analyte. Sensing apparatuses that find use, e.g., in practicing the methods of the present disclosure, are also provided.

15 Claims, 9 Drawing Sheets

(56) References Cited

OTHER PUBLICATIONS

Han & Lo (2012) "Landscape of EGFR signaling network in human cancers: biology and therapeutic response in relation to receptor subcellular locations" Cancer Lett. 318:124-134.
Heath et al. (2016) "Single-cell analysis tools for drug discovery and development" Nat. Rev. Drug Discov. 15:204-216.
Kang et al. (2016) "Single cell-resolution western blotting" Nat. Protoc. 11:1508-1530.
Li et al. (2015) "Multiple effects of IL-21 on human NK cells in ex vivo expansion" Immunobiology. 220:876-888.
Ozel et al. (2015) "Single-cell intracellular nano-pH Probes" RSC Adv. 5:52436-52443.
Peck (2006) "Analysis of protein phosphorylation: methods and strategies for studying kinases and substrates" Plant J. Cell Mol. Biol. 45:512-522.
Rebe et al. (2013) "STAT3 activation" JAK-STAT. 2:e23010-1-e23010-10.
Samsonov et al (2012) "Detection of Endogenous Pathway Activity in Novel Reporter Cell Lines" Biowire Spring. https://www.sigmaaldrich.com/technical-documents/articles/biowire/detection-of-endogenous-pathway-activity.html.
Sendra et al. (2013) "Detection and isolation of auto-reactive human antibodies from primary B cells" Methods. 64(2):17 pages. doi:10.1016/j.ymeth.2013.06.018.
Umehara et al. (2009) "Label-free biosensing with functionalized nanopipette probes" PNAS. 106(12):4611-4616.
Wan et al. (2015) "Opposing roles of STAT1 and STAT3 in IL-21 function in CD4+ T cells" Proc. Natl. Acad. Sci. U.S.A.112:9394-9399.
Wang et al. (2013) "STAT3 activation in response to IL-6 is prolonged by the binding of IL-6 receptor to EGF receptor" Proc. Natl. Acad. Sci. U.S.A. 110:16975-16980.
Yahata et al. (2003) "Nuclear Translocation of Phosphorylated STAT3 Is Essential for Vascular Endothelial Growth Factor-induced Human Dermal Microvascular Endothelial Cell Migration and Tube Formation" J. Biol. Chem. 278:40026-40031.
Zhu et al. (2013) "pSTAT3: a target biomarker to study the pharmacology of the anti-IL-21 R antibody ATR-107 in human whole blood" J. Transl. Med. 11:65, 9 pages.

* cited by examiner

A

B

METHODS FOR SIMULTANEOUS DETECTION OF ANALYTES AND APPARATUSES FOR PRACTICING SAME

CROSS-REFERENCE TO RELATED APPLICATIONS

This application claims the benefit of U.S. Provisional Patent Application No. 62/629,547, filed Feb. 12, 2018, which application is incorporated herein by reference in its entirety.

INTRODUCTION

One of the major challenges in drug discovery and diagnostics of disease has been understanding the complex nature of cell populations within tissues. This complexity motivated the development of several tools for single-cell genomics, transcriptomics and proteomic analysis. Most quantification methods are performed over a large population of cells and then averaged to calculate significance of the targeted protein being studied. However, tissues and cell populations are non-homogenous. Drug resistance, for example, may arise in individual cells that eventually take over a population. The surveillance of single cells has become increasingly important in the understanding of disease progression. From initial efforts to observe a single kind of molecule within a single cell, researchers have progressed in recent years to multiplex single-cell proteomics which typically employ flow cytometry-based fluorescent activated sorting (FACS) as an interface[1]. Some of the recent single cell proteomics techniques incorporate single cell westerns (ScWesterns), microengraving techniques, single-cell barcode chips (SCBCs) and mass cytometry. The majority of these techniques analyze soluble, selected proteins and are not amenable to quantifying intracellular proteins from a single living cell over a course of time[1-4].

Current technologies to investigate proteins in a single cell utilize destructive experimental procedures and do not allow continuous monitoring of an intact single cell. An extensively used approach to study single cell proteins is via fluorescent probes. These probes are essentially designed to be used in homogenous cell lines without having sufficient knowledge of their effect on regular cell metabolic activities.

SUMMARY

Provided are methods for simultaneously detecting analytes. The methods include exposing a tip of a nanosensor to a biological sample, measuring ionic current flow through the nanosensor tip to detect a first analyte and a second analyte in the biological sample, and distinguishing the first analyte from the second analyte based on a first diffusion limited current peak resulting from binding of a first specific binding member to the first analyte being distinguishable from a second diffusion limited current peak resulting from binding of a second specific binding member to the second analyte. Sensing apparatuses that find use, e.g., in practicing the methods of the present disclosure, are also provided.

DETAILED DESCRIPTION

Figure 1:
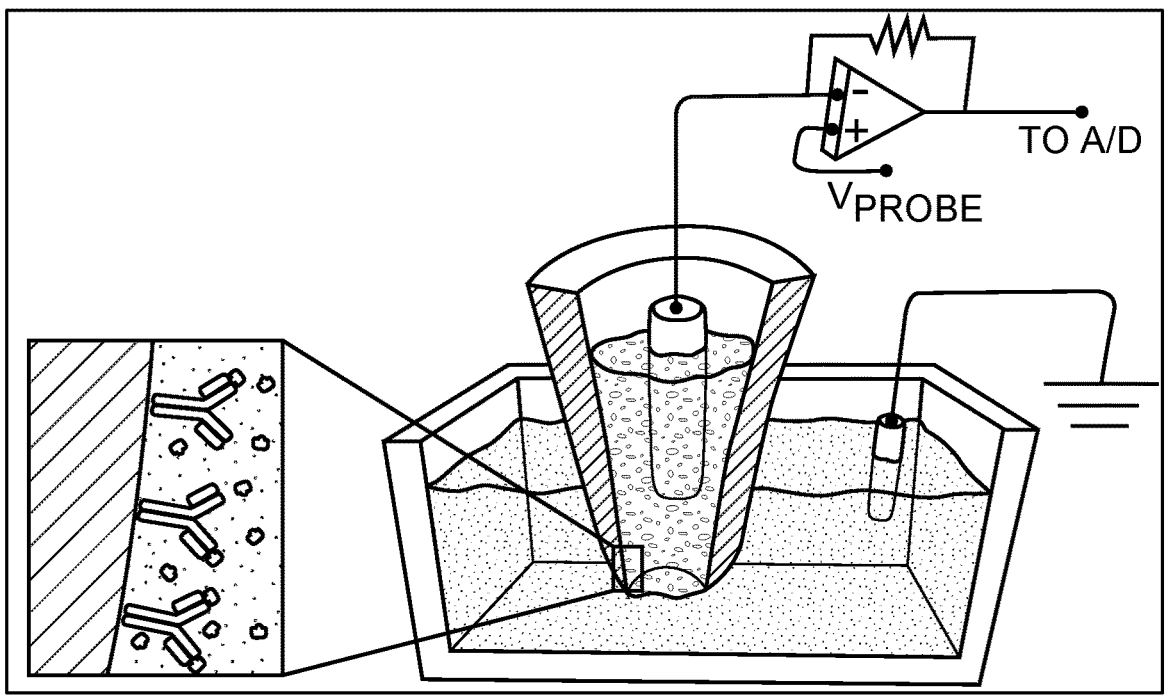
FIG. 1 Schematic of single-cell nanosensing and square wave voltammmogram. In this example, the nanosensor is a nanopipette. Panel A: Illustration of the nanopipette surface coated with antibody; upon penetration into a single cell, the nanosensor antibodies interact with their targets and produces unique current signature peaks for each protein. The schematic shows a two-electrode set-up connected to a potentiostat. A platinum wire placed in the nanopipette filled with an electrolyte serves as a working electrode with a Ag/AgCl electrode placed in the cell media serving as a reference electrode. Panel B: Square-wave voltammogram of 830 ng/ml GFP using nanopipette sensing technology. GFP shows a diffusion limited current peak at −200 mV vs Ag/AgCl based on the GFP:GFP antibody binding. Voltage-clamp conditions: square-wave form potential sweep: −800 mV to 400 mV vs Ag/AgCl; scan rate: 25 mV/s. Blank: 0.01 M PBS at pH 7.4.
Figure 1:
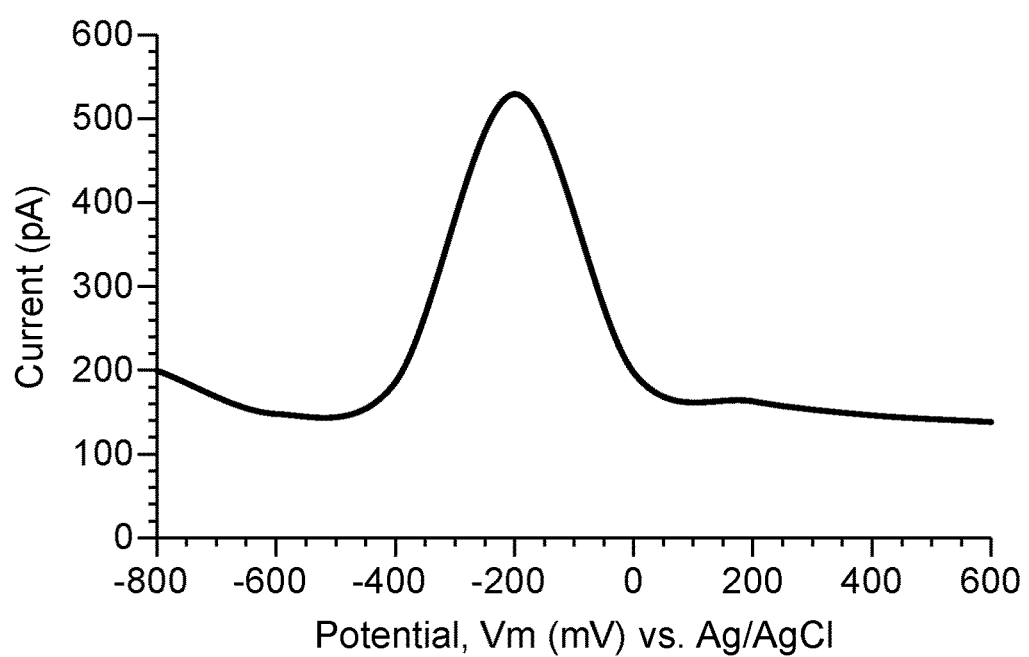

Provided are methods for simultaneously detecting analytes. The methods include exposing a tip of a nanosensor to a biological sample, measuring ionic current flow through the nanosensor tip to detect a first analyte and a second analyte in the biological sample, and distinguishing the first analyte from the second analyte based on a first diffusion limited current peak resulting from binding of a first specific binding member to the first analyte being distinguishable from a second diffusion limited current peak resulting from binding of a second specific binding member to the second analyte. Sensing apparatuses that find use, e.g., in practicing the methods of the present disclosure, are also provided.

Before the methods and apparatuses of the present disclosure are described in greater detail, it is to be understood that the methods and apparatuses are not limited to particular embodiments described, as such may, of course, vary. It is also to be understood that the terminology used herein is for the purpose of describing particular embodiments only, and is not intended to be limiting, since the scope of the methods and apparatuses will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and apparatuses. The upper and lower limits of these smaller ranges may independently be included in the smaller ranges and are also encompassed within the methods and apparatuses, subject to any specifically excluded limit in the stated range. Where the stated range includes one or both of the limits, ranges excluding either or both of those included limits are also included in the methods and apparatuses.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and apparatuses belong. Although any methods and apparatuses similar or equivalent to those described herein can also be used in the practice or testing of the methods and apparatuses, representative illustrative methods and apparatuses are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods and apparatuses are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and apparatuses, which are, for clarity, described in the context of separate embodiments, may also be provided in combination in a single embodiment. Conversely, various features of the methods and apparatuses, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and apparatuses and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods and apparatuses. Any recited method can be carried out in the order of events recited or in any other order that is logically possible.

Methods

As summarized above, the present disclosure provides methods for simultaneous detection of analytes. The methods employ a nanosensor including a tip having a nanoscale-sized opening. The tip is functionalized with two or more specific binding members for binding to respective analytes. Ionic current flowing through the nanosensor tip is measured such that binding of the two or more specific binding members to their respective analytes may be detected. The methods and sensing apparatuses of the present disclosure are based on the unexpected finding that binding of a first specific binding member to its respective analyte may be distinguished from binding of a second specific binding member to its respective analyte based on corresponding non-overlapping diffusion limited current peaks derived from the measured current flow through the nanoscale-sized tip of the nanosensor.

As such, in certain aspects, provided are methods for simultaneously detecting a first analyte and a second analyte in a biological sample. Such methods include exposing a tip of a nanosensor to the biological sample, where the nanosensor defines an internal volume communicating with the biological sample via a nanoscale-sized opening of the tip, where the tip is functionalized with a first specific binding member for binding to the first analyte and a second specific binding member for binding to the second analyte. The nanosensor is part of a sensing apparatus that includes a first electrode in contact with an electrolyte present within the internal volume of the nanosensor, a second electrode in contact with an electrolyte present on a side of the nanoscale-sized opening opposite the electrolyte present within the internal volume of the nanosensor, a circuit for controlling a voltage between the first and second electrodes, and a current detecting circuit adapted to measure ionic current flowing through the nanoscale-sized opening of the tip between the first electrode and the second electrode. The method further includes applying a potential difference between the first electrode and the second electrode, measuring ionic current flow through the nanosensor tip to detect the first analyte and the second analyte in the biological sample, and distinguishing the first analyte from the second analyte based on a first diffusion limited current peak resulting from binding of the first specific binding member to the first analyte being distinguishable from a second diffusion limited current peak resulting from binding of the second specific binding member to the second analyte.

Details regarding nanosensors and sensing apparatuses which may be employed to practice the methods of the present disclosure are provided in the Sensing Apparatuses section herein.

The first and second analytes may be any analytes of interest suspected of being present in the biological sample. In certain aspects, the first and second analytes are independently selected from a polymer, a protein, a nucleic acid, a polysaccharide, and a small molecule.

Proteins of interest include, but are not limited to, proteins found in the nucleus (e.g., histones, polymerases, transcription factors, DNA-modifying proteins, co-activators, chromatin remodelers, histone acetyltransferases, histone deacetylases, kinases, methylases, and the like); cytosol (e.g., cytosolic proteins that function in signal transduction pathways, including G proteins, kinases, dephosphorylases, and the like); cell membrane associated proteins (e.g., cell surface proteins, integrins, receptor tyrosine kinases, G-protein-coupled receptors, cell surface receptors, membrane channel proteins, and the like, including any protein present on the surface of a prokaryotic or eukaryotic cell); extracellular proteins (e.g., extracellular signalling proteins (e.g., cell surface receptor ligands such as growth factors, cytokines, and the like), extracellular matrix (ECM) proteins, and the like).

Nucleic acids of interest include DNA (e.g., genomic DNA, mitochondrial DNA, cell-free DNA, and the like) and RNA. RNAs of interest include, but are not limited to, messenger RNA (mRNA), microRNA (miRNA), small interfering RNA (siRNA), transacting small interfering RNA (ta-siRNA), natural small interfering RNA (nat-siRNA), ribosomal RNA (rRNA), transfer RNA (tRNA), small nucleolar RNA (snoRNA), small nuclear RNA (snRNA), long non-coding RNA (lncRNA), non-coding RNA (ncRNA), transfer-messenger RNA (tmRNA), precursor messenger RNA (pre-mRNA), small Cajal body-specific RNA (scaRNA), piwi-interacting RNA (piRNA), endoribonuclease-prepared siRNA (esiRNA), small temporal RNA (stRNA), signal recognition RNA, telomere RNA, ribozymes, or any combination of RNA types thereof or subtypes thereof.

Non-limiting examples of polysaccharides include homopolysaccharides, heteropolysaccharides, cell-surface polysaccharides, starches, glycogen, cellulose, chitin, and the like.

By "small molecule" is meant a compound having a molecular weight of 1000 atomic mass units (amu) or less. In some embodiments, the small molecule is 750 amu or less, 500 amu or less, 400 amu or less, 300 amu or less, or 200 amu or less. In certain aspects, the small molecule is not made of repeating molecular units such as are present in a polymer. Small molecules of interest include glucose, ketones (e.g., betahydroxybutyrate), small molecule therapeutic drugs, small molecule drugs of abuse, small molecule toxins, heavy metals (e.g., toxic heavy metals), small molecule pesticides, small molecule allergens, and the like.

In some embodiments, the methods employ a nanosensor having a tip functionalized with n specific binding members for binding to n analytes, where n is an integer from 2 to 10, e.g., from 2 to 9, from 2 to 8, from 2 to 7, from 2 to 6, from 2 to 5, from 2 to 4, or from 2 to 3.

The biological sample may be any biological sample of interest, including but not limited to, a single cell (e.g., a single living cell); a cell lysate; proteins and/or nucleic acids obtained (e.g., isolated) from a single cell, tissue, or organism of interest; cell or tissue culture medium; biological fluid (e.g., blood, serum, plasma, saliva, sputum, urine, semen, or the like); an environmental sample (e.g., ground water, surface water, waste water, municipal water, well water, atmospheric water, a soil sample, and the like); etc.

In some embodiments, the biological sample is from a mammal, which term is used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the biological sample is from a human.

In certain aspects, the biological sample is a single cell, or a biological sample obtained from one or more cells, e.g., proteins and/or nucleic acids obtained (e.g., isolated) from one or more cells. Cells of interest include eukaryotic cells, such as mammalian cells, insect cells, yeast cells; and prokaryotic cells, such as bacterial cells.

In certain aspects, the biological sample is a single mammalian cell, or proteins and/or nucleic acids obtained (e.g., isolated) from one or more mammalian cells. Mammalian cells of interest include primary cells as well as mammalian cell lines, e.g., immortalized mammalian cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Yeast cells of interest include, but are not limited to, one or more cells from *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia*

*methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Prokaryotic cells of interest include, but are not limited to, one or more cells from *Escherichia coli, Lactobacillus* sp., *Salmonella* sp., *Shigella* sp., and the like. Examples of *Salmonella* strains include, but are not limited to, *Salmonella typhi* and *S. typhimurium*. Suitable *Shigella* strains include, but are not limited to, *Shigella flexneri, Shigella sonnei*, and *Shigella disenteriae*. Non-limiting examples of other bacteria include *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like.

In some embodiments, the first and/or second analyte is a pathogen. Pathogens of interest include, but are not limited to, viral pathogens, bacterial pathogens, amoebic pathogens, parasitic pathogens, and fungal pathogens. The first and/or second analyte may be a pathogen-specific analyte, e.g., an analyte specific for a particular pathogen the detection of which is indicative of the presence of the pathogen in the biological sample.

By "specific binding member" is meant one member of a pair of molecules that have binding specificity for one another. One member of the pair of molecules may have an area on its surface, or a cavity, which specifically binds to an area on the surface of, or a cavity in, the other member of the pair of molecules. Thus, the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less. Such affinities may be readily determined using conventional techniques, such as by equilibrium dialysis; by using surface plasmon resonance (SPR) technology (e.g., the BIAcore 2000 instrument, using general procedures outlined by the manufacturer); or by radioimmunoassay.

In certain aspects, the first specific binding member and the second specific binding member are independently selected from a polymer, a protein, a nucleic acid, an aptamer, and a chelating agent. In some embodiments, at least one of the first specific binding member and the second specific binding member is a protein selected from an antibody, a receptor, a ligand, a nucleic acid-binding protein (e.g., a transcription factor, a polymerase, a nuclease, and the like), and an enzyme.

The term "antibody" includes antibodies or immunoglobulins of any isotype (e.g., IgG (e.g., IgG1, IgG2, IgG3, or IgG4), IgE, IgD, IgA, IgM, etc.), whole antibodies (e.g., antibodies composed of a tetramer which in turn is composed of two dimers of a heavy and light chain polypeptide); single chain antibodies; fragments of antibodies (e.g., fragments of whole or single chain antibodies) which retain specific binding to the corresponding analyte, including, but not limited to single chain Fv (scFv), Fab, (Fab')$_2$, (scFv')$_2$, and diabodies; chimeric antibodies; monoclonal antibodies, human antibodies, humanized antibodies; and fusion proteins including an antigen-binding portion of an antibody and a non-antibody protein. The antibodies may be further conjugated to other moieties, such as members of specific binding pairs, e.g., biotin (member of biotin-avidin specific binding pair), and the like.

In some embodiments, when the first analyte is a protein, the first specific binding member specifically binds a modified form of the protein. In certain aspects, the modified form of the protein is a post-translational modification. Post-translational modifications (PTMs) increase the functional diversity of the proteome by the covalent addition of functional groups or proteins, proteolytic cleavage of regulatory subunits, etc. Post-translational modifications of interest include, but are not limited to, phosphorylation, glycosylation, ubiquitination, nitrosylation, methylation, acetylation, lipidation, and proteolysis.

In certain aspects, when the first specific binding member specifically binds a modified form of the protein analyte, the second specific binding member binds a corresponding protein lacking the modification. For example, the second specific binding member may bind the protein analyte regardless of whether the protein analyte includes the modification. Alternatively, the second specific binding member may specifically bind the corresponding protein lacking the modification—that is, the second specific binding member does not bind the protein analyte having the modification. By way of example, and as demonstrated in the Experimental section herein, the methods and sensing apparatuses of the present disclosure enable the simultaneous detection of a protein having a modification and the corresponding protein lacking the modification. In the particular example provided in the Experimental section, an example method and sensing apparatus of the present disclosure enables the simultaneous detection of a phosphorylated protein analyte (pSTAT3) and the corresponding non-phosphorylated protein analyte (npSTAT3). In some embodiments, total protein analyte levels may be determined using a specific binding member (e.g., antibody) that binds to the protein regardless of the modification, while a second specific binding member that specifically binds the modified form of the protein may be employed to determine the proportion of the total protein analyte level that includes the modification.

Exposing the tip of the nanosensor to the biological sample includes exposing at least a portion of the tip functionalized with the first and second specific binding members to the biological sample. The biological sample may be a fluid or substantially fluid sample (e.g., a cell lysate, a fluid sample that includes proteins and/or nucleic acids obtained (e.g., isolated) from one or more cells of interest), and exposing the tip of the nanosensor to the biological sample may include inserting at least a portion of the tip functionalized with the first and second specific binding members into the fluid or substantially fluid sample.

In some embodiments, when the biological sample is a single cell (e.g., a single living cell), exposing the tip of the nanosensor to the biological sample includes inserting at least a portion of the tip functionalized with the first and second specific binding members into the cell. Inserting the tip into the cell may be non-specific—that is, without regard to the location of the cell to which the tip is inserted. In other aspects, the tip is inserted into a pre-selected compartment of the cell. The pre-selected compartment is a compartment of interest that will vary depending upon the type of analytes and biological processes of interest to the practitioner of the methods. In some embodiments, the pre-selected compartment is the cytoplasm of the cell. In eukaryotic cells, the cytoplasm includes all of the material inside the cell and outside of the nucleus. In certain aspects, the pre-selected compartment is the cytosol of the cytoplasm—that is, the part of the cytoplasm that is not held by any organelles in the cell. In some embodiments, the pre-selected compartment is a cytoplasmic organelle, which is any organelle inside the cell other than the nucleus. The cytoplasmic organelle may be, e.g., a mitochondrian, chloroplast, lysosome, Golgi apparatus, endoplasmic reticulum (rough or smooth endoplasmic reticulum), vacuole, or the like. In certain aspects, the pre-selected compartment is the nucleus.

The sensing apparatus may include one or more components to facilitate exposing at least a portion of the tip functionalized with the first and second specific binding members to the biological sample. For example, the sensing apparatus may include a y, xy, or xyz controller operably coupled to the nanosensor for effecting mechanical movements of the nanosensor (e.g., in submicron y, xy and/or xyz steps) for positioning at least a portion of the tip functionalized with the first and second specific binding members to the biological sample or pre-selected location thereof. Such a controller may include electronic controls for controlling the mechanical movements according to user defined and/or automated control. In some aspects, the mechanical movement of the nanosensor is controlled by a signal generated by the ionic current flow between the first and second electrodes. Such a controller may be coupled to a device that can image surfaces of biological samples of interest (e.g., single cells) with high resolution, e.g., a scanning ion conductance microscopy (SICM) device. SICM is a form of scanning probe microscopy (SPM) that enables high resolution imaging of soft surfaces without contact or force interaction and in the normal liquid environment of the subject, e.g., single cell. Further details regarding the use of SICM to precisely position the tip of a nanosensor at a desired location of a biological sample (e.g., within a cell or pre-selected location therein) may be found, e.g., in US2016/0032275, the disclosure of which is incorporated herein by reference in its entirety for all purposes.

As summarized above, the methods of the present disclosure include applying a potential difference between the first electrode and the second electrode. The potential difference results in ionic current flow through the nanosensor tip. Detectable changes in the ionic current flow corresponding to the binding of the first and second specific binding members to the first and second analytes (respectively) enables detection of binding events between the specific binding members and their corresponding analytes.

In some embodiments, applying a potential difference between the first electrode and the second electrode includes applying a square wave potential between the first electrode and the second electrode. As such, the methods may employ square wave voltammetry, a form of linear sweep in which the potential is varied as a square wave and the current is measured at the end of each half-wave, just prior to potential change. Such methods may include producing one or more square wave voltammograms which depict first and second diffusion limited current peaks corresponding to binding interactions between the first and second specific binding members with their corresponding analytes. Square wave voltammograms produced according to embodiments of the methods and sensing apparatuses of the present disclosure are shown in FIGS. 1-5. Shown in FIG. 5, for example, are non-overlapping diffusion current peaks corresponding to the binding of an anti-STAT3 antibody to STAT3 and an anti-phosphorylated STAT3 antibody to phosphorylated STAT3 (pSTAT3). In certain aspects, the methods include recording one or more square wave voltammograms and calculating the concentrations of the first and second analytes based on the current responses, e.g., diffusion limited current peaks.

In certain aspects, when the methods include applying a square wave potential between the first electrode and the second electrode, the square wave potential is in the range of from −5000 mV to +5000 mV, such as from −4000 mV to +4000 mV, −3000 mV to +3000 mV, −2000 mV to +2000 mV, or −1000 mV to +1000 mV. In one example, the square wave potential is in the range of from −1000 mV to +400 mV.

The methods may employ any type of nanosensor that defines an internal volume communicating with the biological sample via a nanoscale-sized opening of the tip. In some embodiments, the nanosensor is a channel that provides communication between a first side of a substrate (e.g., membrane) and a second side of the substrate. The channel may have any suitable shape, including but not limited to a cylindrical shape, a conical shape, or the like.

In certain aspects, the nanosensor is a nanopipette. By "nanopipette" is meant a pipette having a tip orifice on the order of tens to hundreds of nanometers and formed using a puller, e.g., a laser-based pipette puller system or using nanofabrication processes. In certain aspects, the methods employ a nanopipette have an inner diameter on the order of from about 20 nm to about 1.0 μm, an outer diameter of from about 0.7 to about 1.5 mm, and a typical length on the order of about 10 nm to about 100 mm.

By "nanoscale-sized opening" is meant the largest linear dimension of the opening of the tip (e.g., diameter in the case of a circular opening) is in the nanoscale range—that is, 1000 nm or less. In any of the methods and sensing apparatuses of the present disclosure, the nanoscale-sized opening (or orifice) of the tip may be from 1 to 1000 nanometers (nm), 3 to 800 nm, 5 to 600 nm, 7 to 600 nm, 8 to 400 nm, or 10 to 200 nm.

Sensing Apparatuses

As summarized above, the present disclosure provides sensing apparatuses. The sensing apparatuses find use, e.g. in practicing the methods of the present disclosure. As such, in certain aspects, the sensing apparatuses of the present disclosure are adapted to perform any of the steps of the methods of the present disclosure in any combination.

In some embodiments, the sensing apparatuses include a nanosensor that includes a tip including a nanoscale-sized opening and functionalized with a first specific binding member for binding to a first analyte and a second specific binding member for binding to a second analyte, and an internal volume which, when in use, is in communication with a biological sample via the nanoscale-sized opening of the tip. Such sensing apparatuses further include a circuit for controlling a voltage between a first electrode configured to contact an electrolyte present within the internal volume of the nanosensor, and a second electrode configured to contact an electrolyte present on a side of the nanoscale-sized opening opposite the electrolyte present within the internal volume of the nanosensor. Such sensing apparatuses further include a current detecting circuit configured to measure ionic current flowing through the nanoscale-sized opening of the tip between the first electrode and the second electrode, and a non-transitory computer-readable medium. The non-transitory computer-readable medium including instructions that, when in use, cause the sensing apparatus to apply a potential difference between the first electrode and the second electrode, measure ionic current flow through the nanosensor tip to detect the first analyte and the second analyte in the biological sample, and distinguish the first analyte from the second analyte based on a first diffusion limited current peak resulting from binding of the first specific binding member to the first analyte being distinguishable from a second diffusion limited current peak resulting from binding of the second specific binding member to the second analyte.

In certain aspects, the non-transitory computer-readable medium includes instructions that, when in use, cause the sensing apparatus to apply a square wave potential between the first electrode and the second electrode. The square wave potential may be in the range of from −5000 mV to +5000 mV, such as from −4000 mV to +4000 mV, −3000 mV to +3000 mV, −2000 mV to +2000 mV, or −1000 mV to +1000 mV. In one example, the square wave potential is in the range of from −1000 mV to +400 mV. As such, the non-transitory computer-readable medium may include instructions that enable to the sensing apparatus to perform square wave voltammetry for nanosensor-based biosensing. According to such aspects, the non-transitory computer-readable medium may further include instructions that, when in use, cause the sensing apparatus to produce one or more square wave voltammograms which depict first and second diffusion limited current peaks corresponding to binding interactions between the first and second specific binding members with their corresponding analytes (see, e.g., FIG. 5). In certain aspects, the methods include recording one or more square wave voltammograms and calculating the concentrations of the first and second analytes based on the current responses, e.g., diffusion limited current peaks.

The first specific binding member and the second specific binding member may bind to any analytes of interest, including any of the analytes described above in the section relating the Methods of the present disclosure. The first specific binding member and the second specific binding member may be any suitable specific binding members, including any of the specific binding members described above in the section relating the Methods of the present disclosure.

By "the tip is functionalized" with first and second specific binding members or "a tip . . . functionalized" with first and second specific binding members is meant the perimeter of the nanoscale-sized opening itself and/or an internal surface of the nanosensor in sufficient proximity to the nanoscale-sized opening includes first and second specific binding members disposed thereon. By "sufficient proximity to the nanoscale-sized opening" is meant the first and second specific binding members are disposed on an internal surface of the nanosensor close enough to the opening such that changes in current flowing through the tip may be detected upon binding of the first and second specific binding members to the first and second analytes, respectively. That is, the functionalization is in sufficient proximity to the opening that first and second diffusion limited current peaks corresponding to binding interactions between the first and second specific binding members to the first and second analytes, respectively, may be obtained.

The tip of the nanosensor may be functionalized with the first and second specific binding members using any convenient approach. In some embodiments, the first specific binding member and/or the second specific binding member is/are directly attached to the perimeter of the nanoscale-sized opening and/or an internal surface of the nanosensor.

In other embodiments, the surface of the nanosensor is chemically modified for linkage (e.g., covalent linkage) of the first and second specific binding members to the surface. In one non-limiting example, the nanosensor (e.g., nanopipette) is made of negatively charged glass or quartz, which is coated with a layer of poly-L-lysine (PLL), thereby altering the charge and supplying amine groups. Next, the surface is treated with a carboxylated polymer such as polyacrylic acid or polymethacrylic acid, containing multiple carboxyl groups. Using EDC/NHS (1-Ethyl-3-(3-dimethylaminopropyl)-carbodiimide/N-Hydroxysuccinimide), a linkage between the surface and added Protein A/G is formed. In the final step, the first and second specific binding members (e.g., proteinaceous first and second specific binding members, such as antibodies) are immobilized onto the chemically modified surface.

In a functionalization approach involving biotinylated specific binding members, the nanosensor surface may be modified with PLL, then with poly(acrylic acid) (PAA), and then surface activated with EDC/NHS solution (e.g., 10 mg/ml in MES buffer). The resulting chemistry may be used to bind streptavidin, which in turn may be used to bind the biotinylated specific binding members (e.g., biotinylated antibodies), thereby functionalizing the tip of the nanosensor with the first and second specific binding members.

The sensing apparatus may further include a controller operably coupled to the nanosensor for effecting mechanical movement of the nanosensor in one or more of the x, y, and z directions, enabling positioning of at least a portion of the tip functionalized with the first and second specific binding members to the biological sample or pre-selected location thereof. Such a controller may include electronic controls for controlling the mechanical movements according to user defined and/or automated control. According to such embodiments, the non-transitory computer-readable may further include instructions that cause the controller to effect mechanical movement of the nanosensor in the desired manner.

In certain aspects, the sensing apparatus further includes a scanning ion conductance microscope (SICM). When the sensing apparatus includes a SICM, the non-transitory computer-readable medium may further include instructions that, when in use, cause the SICM of the sensing apparatus to image the topography of the biological sample or component thereof (e.g., a single cell, such as a single living cell) and enable positioning of the nanosensor tip in the biological sample or a desired location therein. For example, when the biological sample is a single cell, the non-transitory computer-readable medium may further include instructions that, when in use, cause the SICM of the sensing apparatus to image the topography of the cell and enable insertion of the nanosensor tip into the cell or pre-selected location/compartment therein, e.g., the cytoplasm or compartment thereof (e.g., cytosol or organelle), or the nucleus.

Any type of nanosensor that defines an internal volume and adapted to communicate with the biological sample via a nanoscale-sized opening of its tip may be implemented in the sensing apparatuses of the present disclosure. In some embodiments, the nanosensor is a channel that provides communication between a first side of a substrate (e.g., membrane) and a second side of the substrate. The channel may have any suitable shape, including but not limited to a cylindrical shape, a conical shape, or the like. In certain aspects, the nanosensor is a nanopipette as described above in the section relating to the Methods of the present disclosure. In certain aspects, the sensing apparatuses include a nanopipette having an inner diameter on the order of from about 0.40 to about 1.0 mm (e.g., about 0.70 mm), an outer diameter of from about 0.7 to about 1.3 mm (e.g., about 1 mm), and a typical length on the order of 5-100 mm.

By "nanoscale-sized opening" is meant the largest linear dimension of the opening of the tip (e.g., diameter in the case of a circular opening) is in the nanoscale range—that is, 1000 nm or less. In any of the methods and sensing apparatuses of the present disclosure, the nanoscale-sized opening (or orifice) of the tip may be from 1 to 1000 nanometers (nm), 3 to 800 nm, 5 to 600 nm, 7 to 600 nm, 8 to 400 nm, or 10 to 200 nm.

The following examples are offered by way of illustration and not by way of limitation.

EXPERIMENTAL

Introduction

While there are biosensors capable of identifying and quantifying proteins, they lack specificity and sensitivity for detecting proteins at a single cell level, while at the same time being non-destructive. Described herein is a multiplex nanosensor platform capable of detecting multiple proteins within a single living cell. As proof of concept, a biotinylated antibody coated nanosensor was employed that not only detects real time changes in protein levels within a cell but also measures protein modifications, including phosphorylation. The multiplex nanosensor produced unique and distinct current signature peaks for each protein. Furthermore, proteins were detected as early as 5 minutes in vivo in a single cell with a lower detection limit at picogram levels. This non-destructive single cell sensor platform is flexible, enables rapid detection, is regenerative, and is readily multiplexed.

In particular, described herein is a novel label-free nanosensor-based system which allows the detection and quantification of intranuclear levels of transcription factors (e.g., STAT3) within a single cell. This technology can identify impairments in protein phosphorylation associated with various human disease states including cancer. These nanosensors can be further applied to study intracellular signaling processes. The data herein indicates the development of a state-of-the-art multiplex protein sensor, providing real-time measurement of multiple proteins and protein modifications including phosphorylation state and the dynamic changes in a single cell with high specificity. The multiplex nanosensor described in this study serves as a platform for development of a fast, compact and easily multiplexed biosensing device to detect various proteins in a variety of biological sample types, including non-destructive single-cell sensing capability.

Interleukin-21, a common gamma-chain cytokine, activates multiple cell signaling pathways, including the JAK-STAT pathway. IL-21 induces phosphorylation of JAK-1 and JAK-3, which in turn leads to phosphorylation and nuclear translocation of STAT3 and plays roles in activation, maturation and proliferation of natural killer (NK) cells as well as other roles in the immune system[11-14]. It is also well known that epidermal growth factor receptor (EGFR) catalyzes the tyrosine phosphorylation of STAT3 in response to epidermal growth factor (EGF)[15,16]. Therefore, as a model system and proof of concept, activation of STAT3 using external stimuli including EGF and IL-21 was chosen for phosphorylation and localization studies using the nanosensing platform of the present disclosure in single NK-92 cells, a clinically used human NK cell line. The approach was adapted for developing a multiplex protein sensor specific for non-phosphorylated STAT3 (npSTAT3) and phosphorylated STAT3 (pSTAT3). Accurate real-time detection of both npSTAT3 and pSTAT3 levels in the cytoplasm and nucleus using the present nanosensing platform can provide biochemical evidence for the prognosis of cancer, viral infections, aid in design of anti-cancer and anti-viral agents, etc.

Example 1—Calibration of Monoplexed and Multiplexed Sensor

Figure 2:
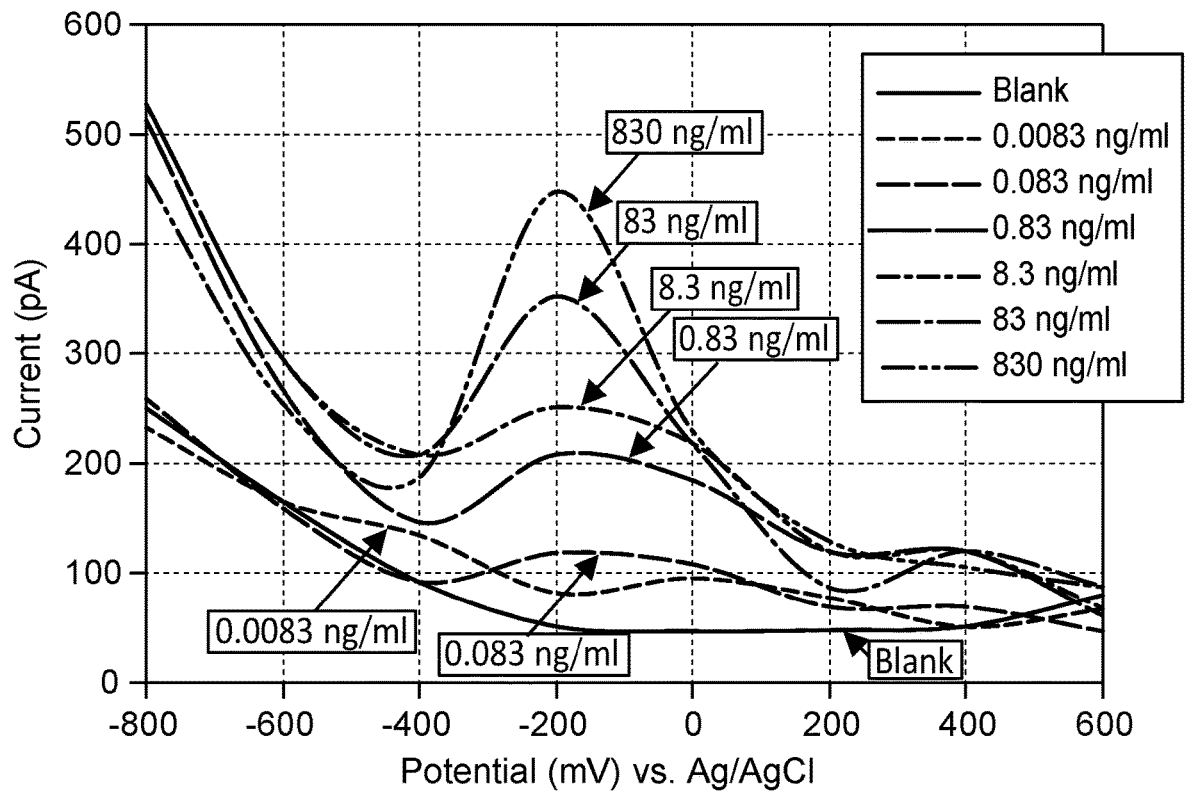
FIG. 2 Square-wave voltammograms for the detection of GFP in the concentration range of 0.0083-830 ng/ml using nanopipette sensing technology. GFP shows a diffusion current peak at −200 mV vs Ag/AgCl based on GFP:GFP antibody binding (Panel A). The calibration curve of GFP in the range of 0.0083-830 ng/ml, including the low level dynamic range (inset) using the monoplexed immunoassay for GFP (Panel B). All measurements were done in triplicate. Voltage-clamp conditions: square-wave form potential sweep: −800 mV to 400 mV vs Ag/AgCl; scan rate: 25 mV/s. Blank: 0.01 M PBS at pH 7.4.
Figure 2:
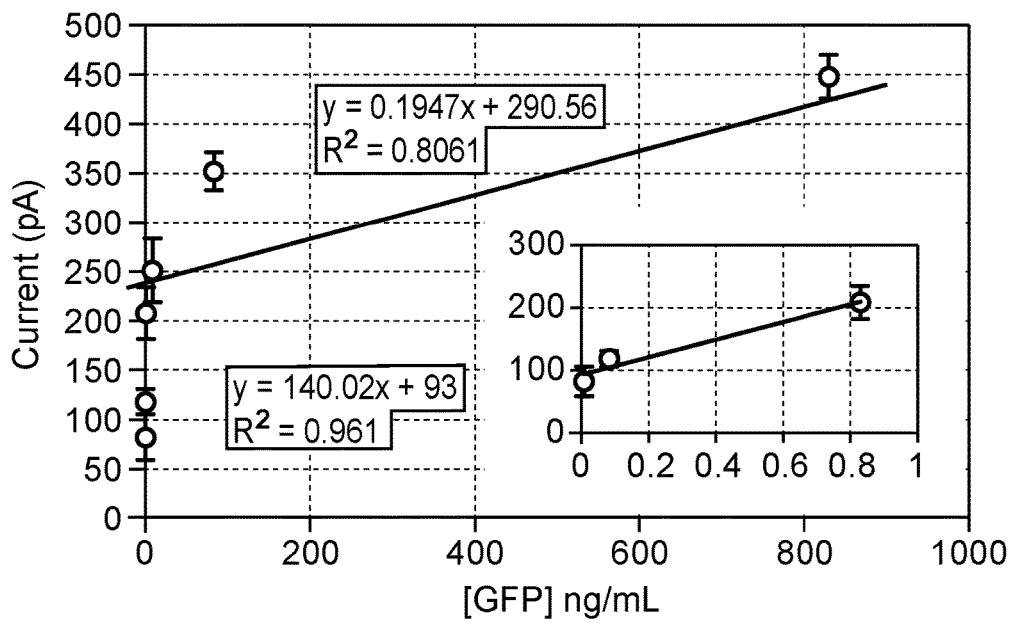

Shown in FIG. 1 is an example square wave voltammogram (SWV) that can be obtained with this novel technique to detect the protein of interest—in this case, GFP and transcription factor, by means of the nanosensor. FIG. 1, panel A, illustrates the binding of antibody to the nanosensor and the signal produced when it binds its target protein when a square wave form potential is applied in the range of −1V to +1V (vs. Ag/AgCl reference electrode) resulting in a change in current at the tip. The specific binding yields an exothermic binding isotherm (enthalpy, $\Delta H=-10$ KCal/mol at 25° C.) due to the formation of an anti-GFP antibody complex on the inner surface of the nanopipette. The exothermic reaction releases energy to form a stable binding of the complex in the form of an electric current. A maximum diffusion current peak appears at −200 mV vs Ag/AgCl using SWV. The calibration curve of GFP was found to be biphasic in the range of 0.0083-830 ng/ml, including the low level dynamic range using a monoplexed immunoassay for GFP (FIG. 2).

Figure 3:
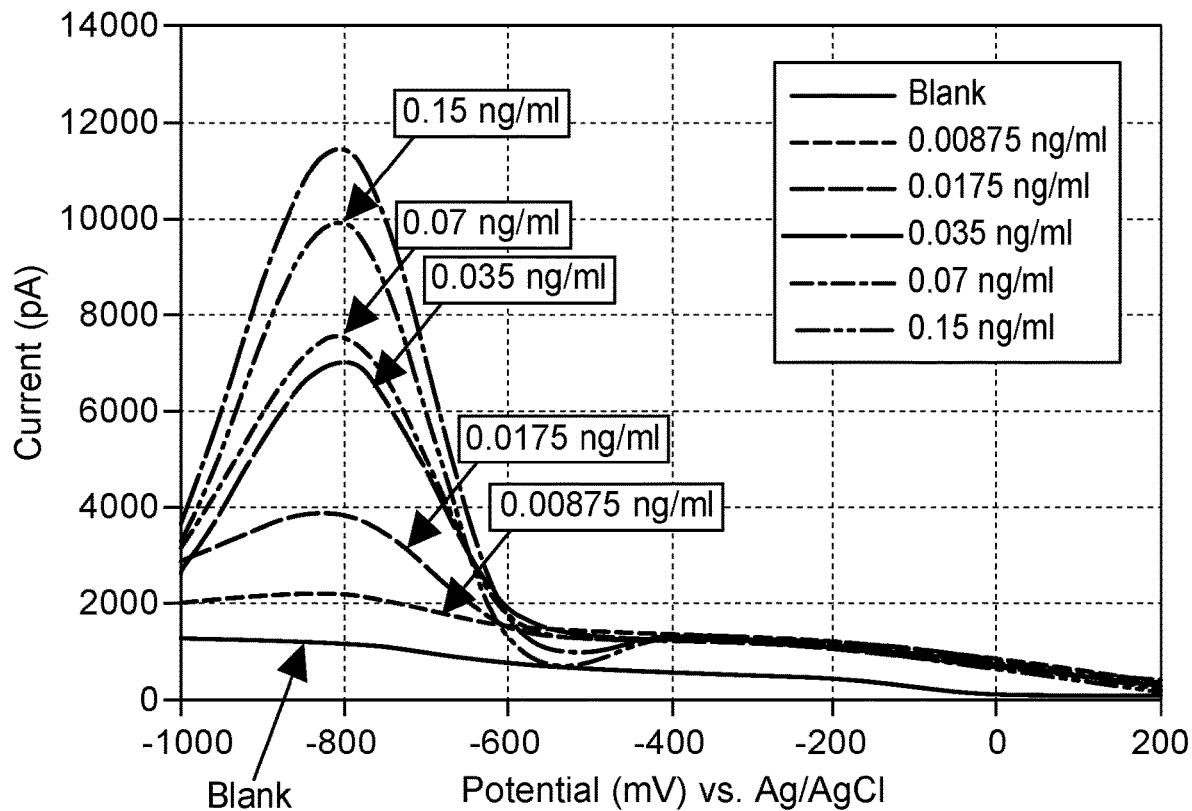
FIG. 3 Square-wave voltammograms for detection of npSTAT3 in the concentration range of 0.0087-0.3 ng/ml using the nanopipette sensing technology. npSTAT3 shows a diffusion current peak at −800 mV vs Ag/AgCl based on the npSTAT3:STAT3 antibody binding. The calibration curve of pSTAT3 is in the range of 0.0087-0.3 ng/ml, including low-level dynamic range using the monoplexed immunoassay for STAT3. All measurements were done in triplicate. Blank: 0.01M PBS at pH 7.4.
Figure 3:
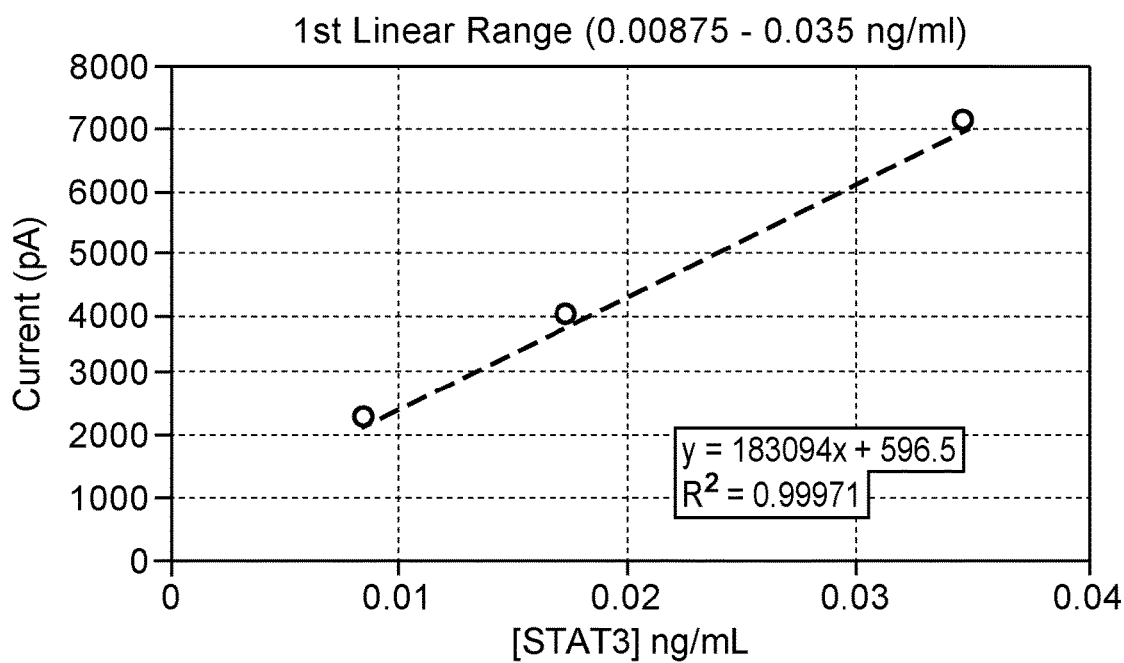
Figure 3:
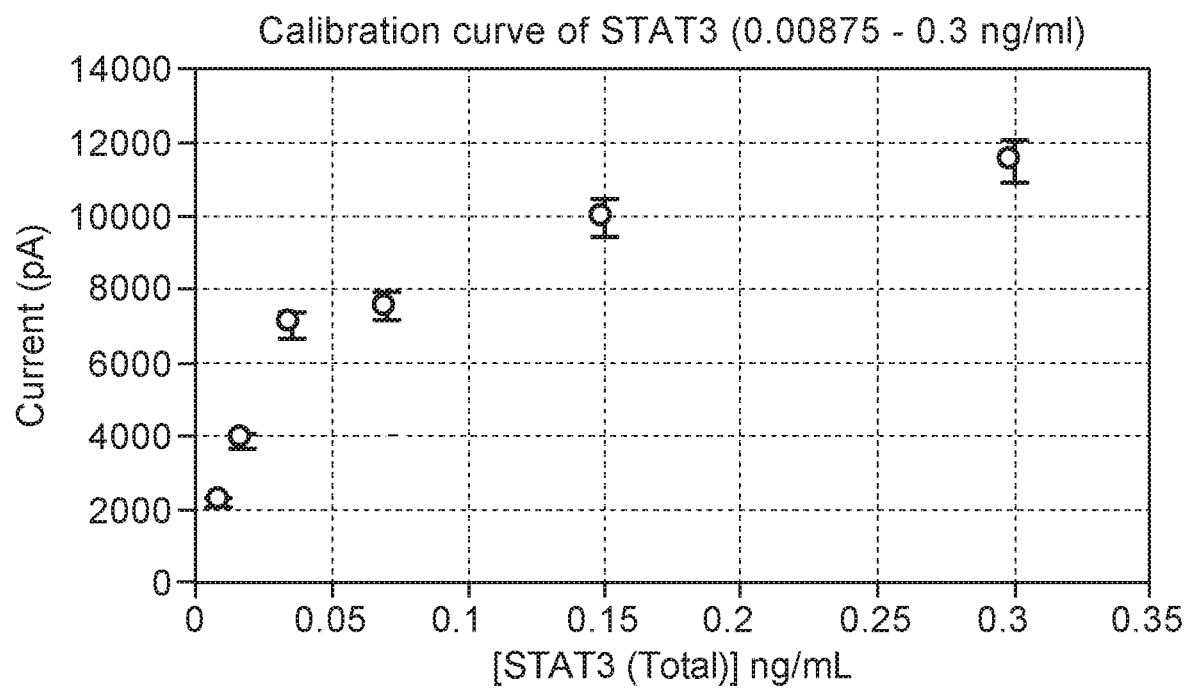
Figure 3:
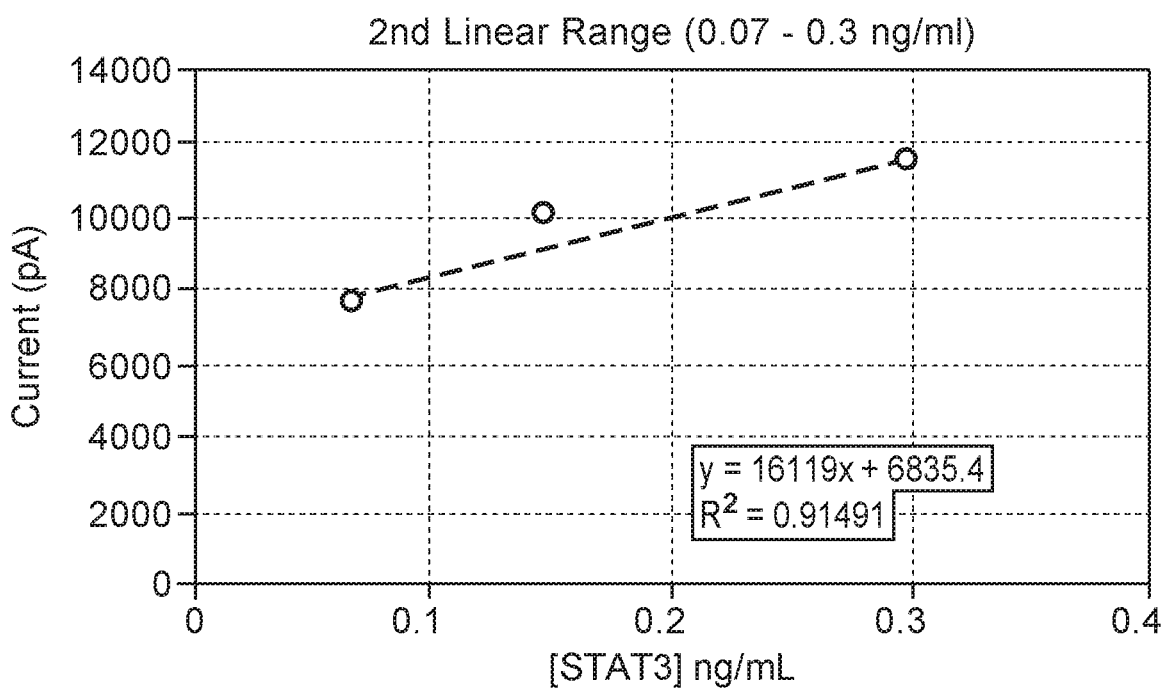
Figure 4:
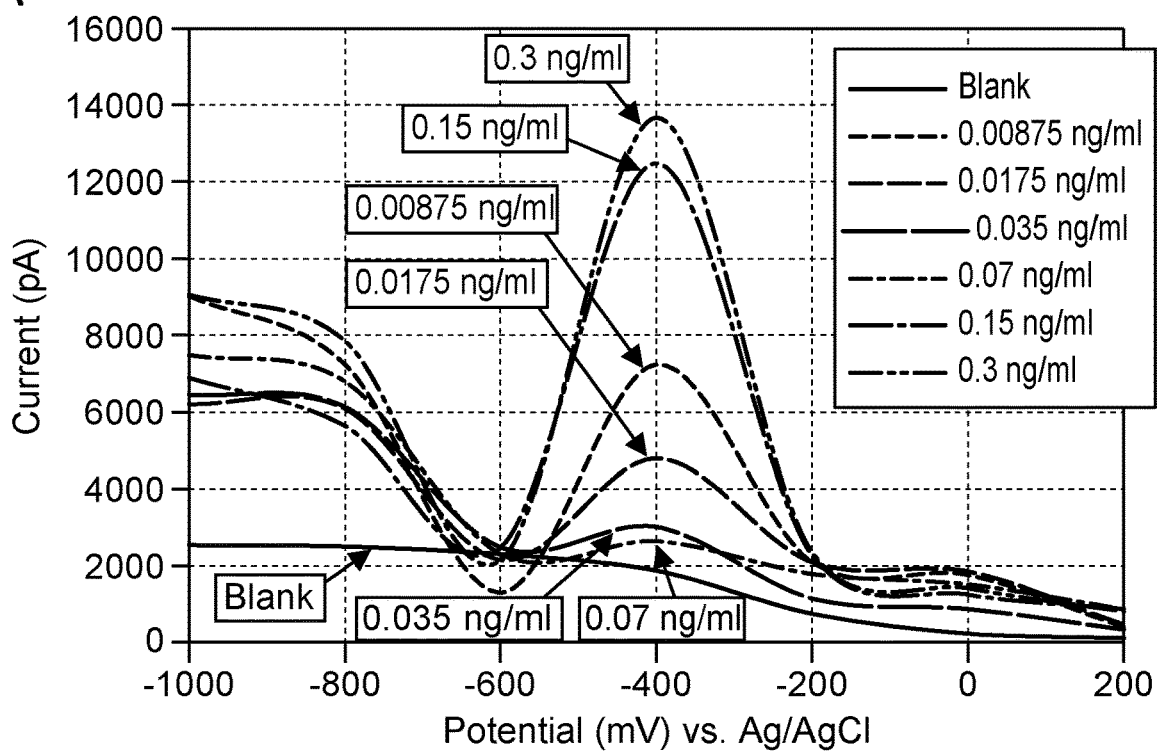
FIG. 4 Square-wave voltammograms for detection of pSTAT3 (pY705) in the concentration range of 0.0087-0.3 ng/ml using the nanopipette sensing technology. pSTAT3 (pY705) shows a diffusion current peak at −400 mV vs Ag/AgCl based on the pSTAT3(pY705):anti-pSTAT3 antibody binding (Panel A). The calibration curve of pSTAT3 is in the range of 0.0087-0.3 ng/ml, including low-level dynamic range (inset) using the monoplexed immunoassay for pSTAT3 (pY705) (Panel B). All measurements were done in triplicate. Blank: 0.01M PBS at pH 7.4.
Figure 4:
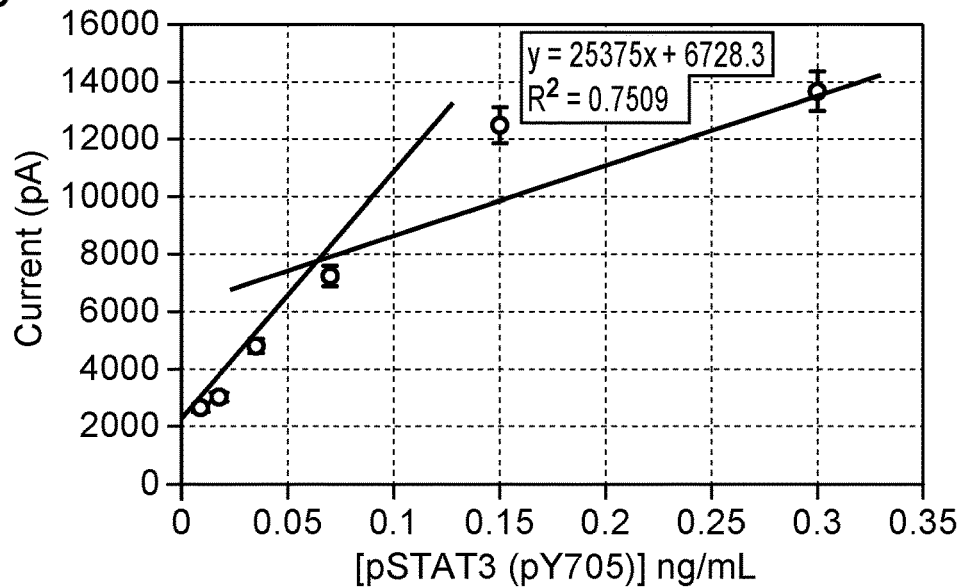
Figure 4:
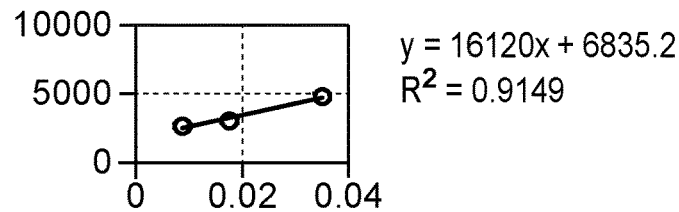
Figure 5:
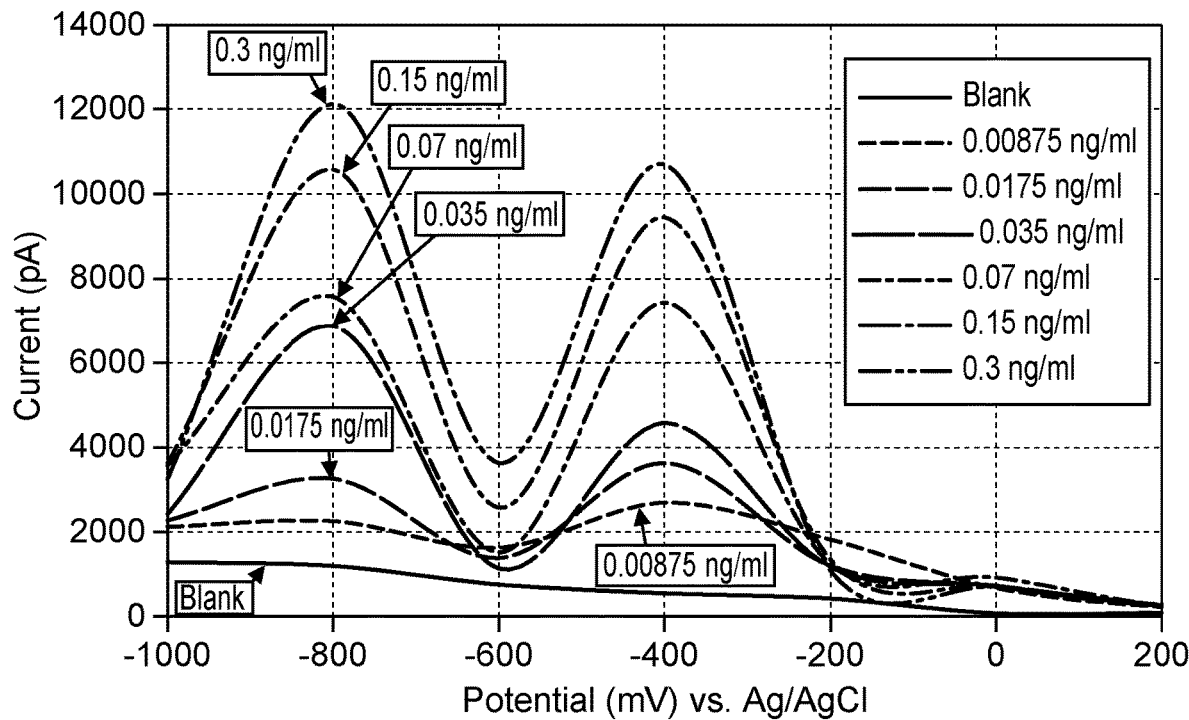
FIG. 5 Calibration curve for simultaneous detection of npSTAT3 (−800 mV) and pSTAT3 (−400 mV) using the multiplexed nanosensor showing non-overlapping distinct peaks for npSTAT3 and pSTAT3 in the concentration range of 0.0087 to 0.3 ng/ml.

Calibration studies for a STAT3 and pSTAT3 nanosensor displayed a maximum diffusion current at −800 mV and −400 mV respectively (FIGS. 3 and 4). The calibration curve of STAT3 and pSTAT3 was found to be in the range of 0.0087-0.3 ng/ml, including low-level dynamic range using the monoplexed immunoassay for STAT and pSTAT3, respectively. Non-overlapping peaks of STAT3 and pSTAT3 were seen in the multiplexed assay when the nanosensor surface was modified with both antibodies (FIG. 5). Results from calibration studies enabled the use of a multiplex sensor for simultaneous detection of multiple proteins in single cells. The limit of detection for each sensor was as low as 8.3 pg/ml.

Figure 6:
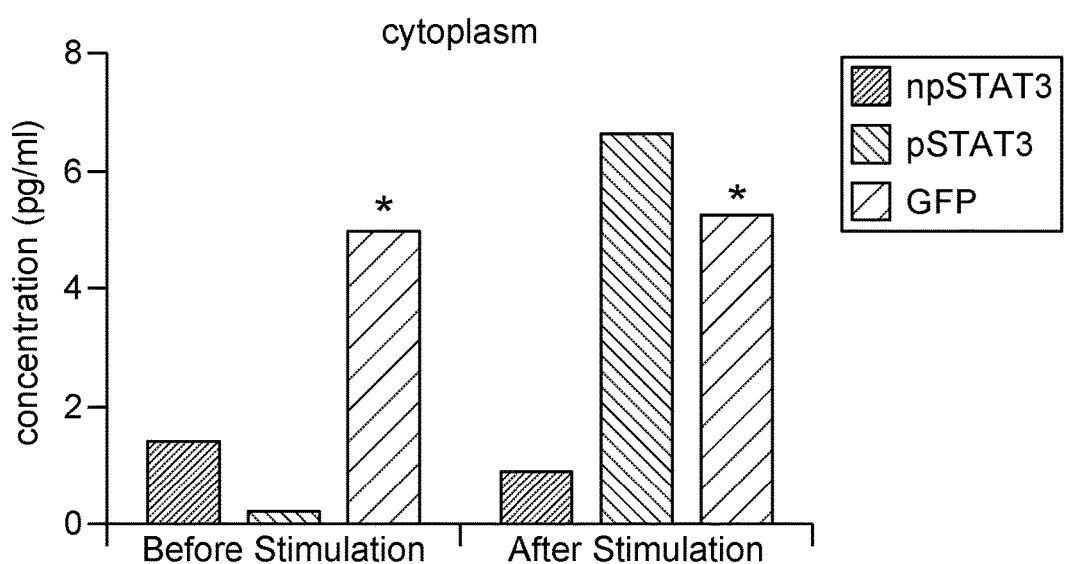
FIG. 6 npSTAT3, pSTAT3 and GFP concentrations were measured in the cytoplasm of HEK-293T cells expressing GFP before and after EGF (200 ng/ml) stimulation using multiplexed nanosensor. * indicates concentration in ng/ml. Concentrations detected for npSTAT3 and pSTAT3 were in the picogram levels.

Example 2—Internal Control Assay: EGF Stimulation does not Affect GFP Concentration in a Single Cell GFP was measured in GFP-expressing HEK single cell using the multiplex sensor before and after stimulation with EGF (200 ng/ml). We found GFP concentration remains constant at ~5 ng/ml before and after stimulation which indicates that EGF stimulation does not affect GFP concentration inside the cell (FIG. 6). Simultaneous measurement of npSTAT3 and pSTAT3 concentration in the same cell showed basal levels of pSTAT3 before activation (FIG. 6). However, after EGF activation, pSTAT3 levels increased 6-fold in the cytoplasm. This shows that EGF stimulation is not generic but induces phosphorylation of only the specific protein of interest as detected by multiplex protein sensor.

Example 3—Activation of Transcription Factor STAT3

Figure 7:
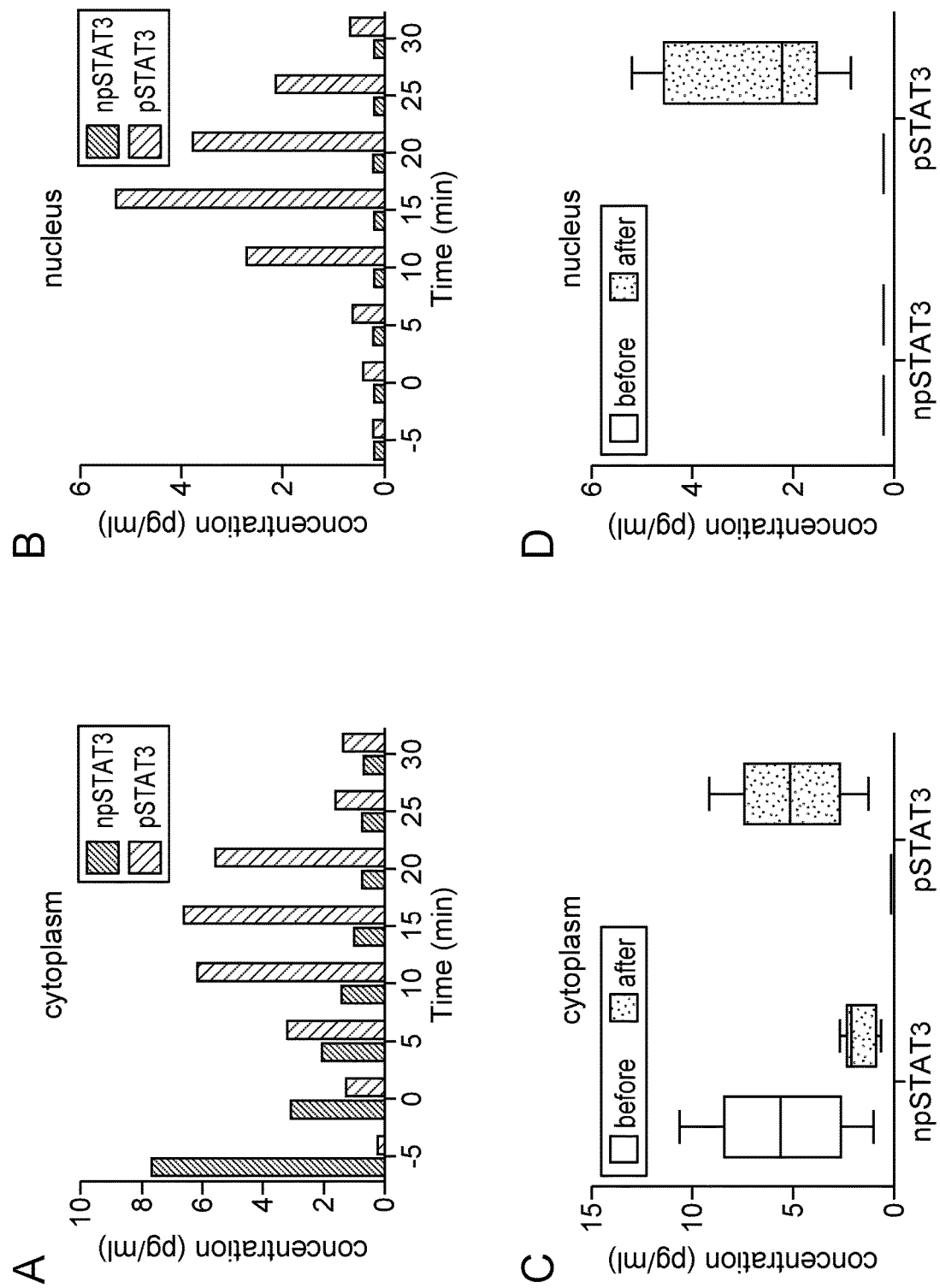
FIG. 7 Measurement of npSTAT3 and pSTAT3 in intact NK-92 cell in cytoplasm (Panel A) and the nuclear region (Panel B) using the multiplexed STAT3 nanosensor employing anti-npSTAT3 (Black bars) and anti-pSTAT3 (grey bars) antibodies. The cells were exposed to 200 ng/ml EGF at time 0. Studies monitoring phosphorylation in the cytoplasm were done on different cells than those monitoring the nuclear region. Box graph (Panel C) and (Panel D) summarizing the average measured intracellular non-phosphorylated STAT3 (npSTAT3) and phosphorylated STAT3 (pSTAT3) in the cytoplasms of five different single NK-92 cells before (white) and after (grey) EGF stimulation in cytoplasm and nucleus region. The boxes show the intervals and the lines within boxes show the average concentration.
Figure 8:
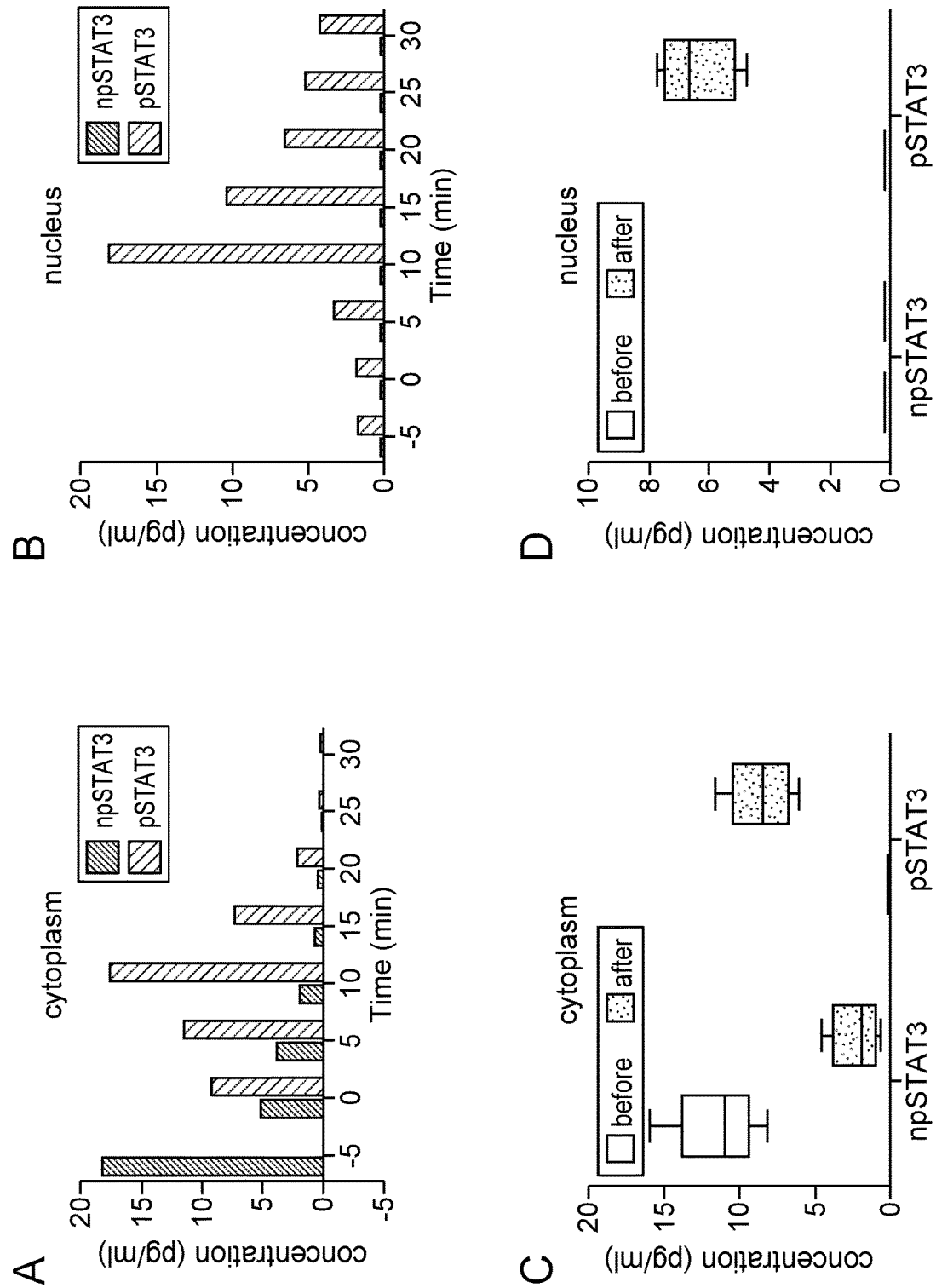
FIG. 8 Measurement of npSTAT3 and pSTAT3 in intact NK-92 cell in cytoplasm (Panel A) and the nuclear region (Panel B) using the multiplexed STAT3 nanosensor employing anti-STAT3 (black bars) and anti-pSTAT3 (grey bars) antibodies. The cells were exposed to 200 ng/ml IL-21 at time 0. Studies monitoring phosphorylation in the cytoplasm were done on different cells than those monitoring the nuclear region. Box graph (Panel C) and (Panel D) summarize the average measured intracellular npSTAT3 and pSTAT3 in the cytoplasms of five different single NK-92 cells before (white) and after (grey) IL-21 stimulation in cytoplasm and nucleus region. The boxes show the intervals and the lines within boxes show the average concentration.

Analysis of non-phosphorylated and phosphorylated products of STAT3 in a single cell was performed before and after activation using two different activation factors. First, NK-92 cells were stimulated using EGF and IL-21 at different times (FIG. 7, panels A and B; FIG. 8, panels A and B). The optimal concentration of each stimulus was obtained from previously reported data, with each activator at a concentration of 200 ng/ml. Next, the intracellular pSTAT3 concentration was measured following stimulation with EGF (FIG. 7) and IL-21 (FIG. 8) in a single NK-92 cell. Basal levels of total STAT3 (no EGF at time −5 min) comprised only npSTAT3 at a concentration of 7.67 pg/ml in the cytoplasm. pSTAT3 was not detected at this time point. Upon stimulation of the cell with EGF at time zero (La, at the time of adding EGF to a cell), a gradual increase in pSTAT3 levels was observed. The level of the phosphorylated form of STAT3 increased as early as 5 minutes following treatment and maximum phosphorylation (6.6 pg/ml pSTAT3) was obtained 15 minutes after stimulation with EGF. Placement of the multiplex sensor near the nucleus of the cell showed a gradual increase in pSTAT3 following EGF stimulation. npSTAT3 was not detected near the nucleus.

Figure 9:
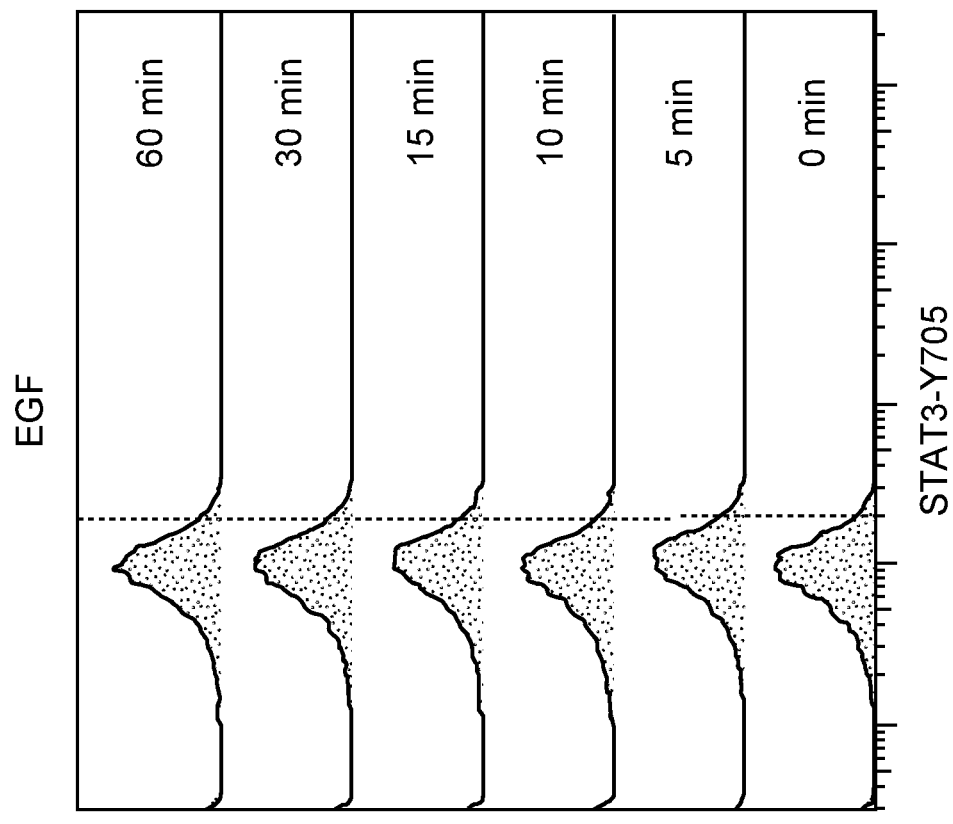
FIG. 9 Flow cytometric analysis of pSTAT3-Tyr705 upon IL-21 (left) and EGF (right) stimulation of NK-92 cells (one representative flow cytometry experiment for each).
Figure 9:
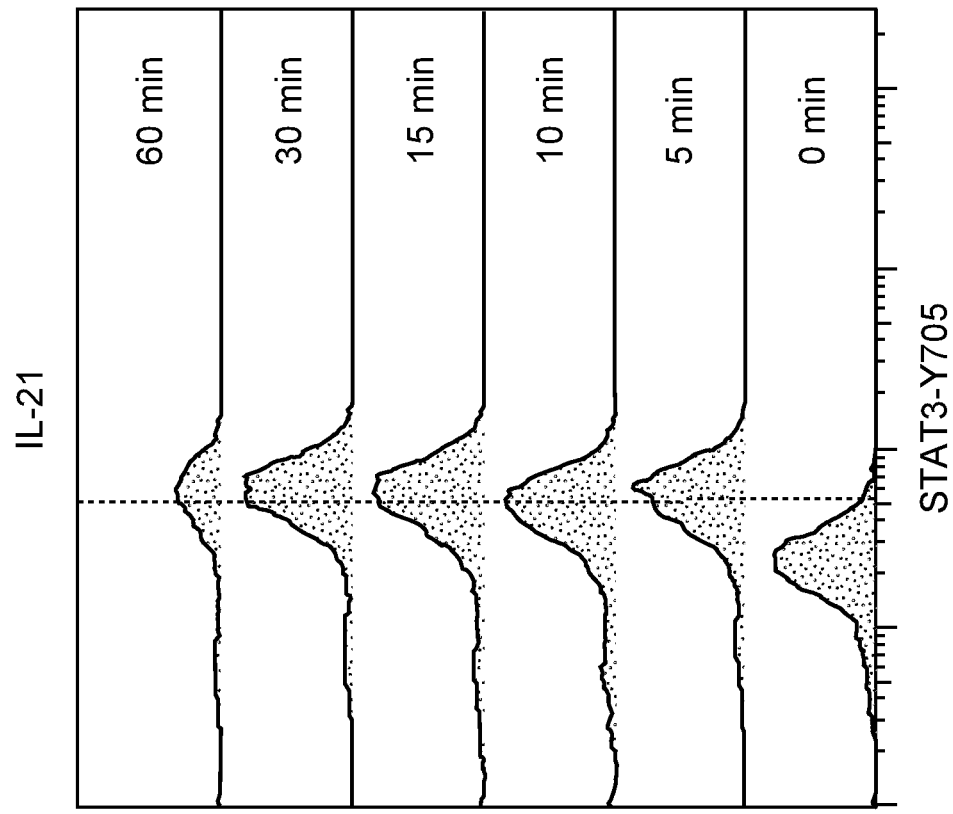

A similar protocol was established to observe STAT3 response following IL-21 treatment of NK-92 cells. As expected, pSTAT3 concentration was amplified with IL-21 stimulation. Increased pSTAT3 levels were observed as early as 5 minutes following treatment with IL-21 (200 ng/ml) and maximum phosphorylation was obtained 10 minutes after stimulation for a single cell in comparison to its unstimulated state (FIG. 8). pSTAT3 levels in cytoplasm reached the highest amount (17.59 pg/ml) after 10 minutes. In the nucleus, 18.23 pg/ml of pSTAT3 was detected after 10 minutes of IL-21 induction. These observations were also confirmed by flow cytometric analysis of pSTAT3-Tyr705 upon IL-21 stimulation of NK-92 cells. Phosphorylation was detectable even after 5 minutes of IL-21 treatment and remained as high at following time points up to 60 minutes of treatment (FIG. 9). The same effect was not observed with EGF even with different doses and different batches of cells. These conditions were considered to represent the baseline to observe any significant difference of STAT3 and pSTAT3 concentration between non-activated NK-92 cells and NK-92 single cells activated by either EGF or IL-21.

Example 4—Multiplex Single-Cell Protein Detection

Having identified optimal conditions for stimulating the NK-92 cell for activation of the nuclear transcription factor pSTAT3, the single cell sensing technique was established. This platform allows the detection and quantitation of nuclear factors at the single cell level in both the cytoplasm and nucleus over a period of time without disrupting the cell. FIG. 7 shows the quantification of npSTAT3 and pSTAT3 measured in four different single cells in the cytoplasm and nucleus 15 min after EGF stimulation. pSTAT3 was below detection level in the cytoplasm before activation with EGF. The average npSTAT3 levels was 5.636 pg/ml. After activation, npSTAT3 fell to a concentration of 1.74 pg/ml and the pSTAT3 concentration increased to 5.08 pg/ml. The values for each cell were in the range of 4 pg/ml to 9.2 pg/ml. pSTAT3 concentration increased 4 fold after activation in cytoplasm. Prior to stimulation, npSTAT3 was detected in the nucleus, and only low levels of pSTAT3 were observed. After EGF activation, about 3-fold increase in pSTAT3 was seen in the nucleus of single cells (FIG. 7, panel B). FIG. 8, panels A and B, show the quantification of STAT3 and pSTAT3 measured in different single cells in the cytoplasm and nuclear region following 10 minutes of IL-21 stimulation.

The example multiplex nanosensor of the present disclosure provided excellent performance and possessed advantages of simplicity, selectivity, reproducibility and reliability for simultaneous detection of STAT3, pSTAT3 and GFP in the concentration range of 8.75 pg/ml to 300 pg/ml with a lower detection limit of 8.3 pg/ml. The method enabled the quantification of multiple intracellular proteins and their phosphorylation state within a single cell over time as well as over two intracellular regions, and represents an important tool in understanding fundamental biochemical process occurring inside a single living cell. Each of the proteins detected gave a non-overlapping unique and distinct peak. The predominance of pSTAT3 in the nuclear region is consistent with the translocation of the activated form of this transcription factor from the cytoplasm to the nucleus.

The nanosensor platform and method described herein is a basis for building other multiplex nanopipette biosensing modules that can be implemented for multiplexed detection of various targets within a single cell. In conclusion, the multiplex nanosensor platform and method of the present disclosure constitutes a powerful tool for detection of protein targets in research, clinical and environmental applications.

Materials and Methods

Reagents and Materials

Poly-L-lysine solution (PLL), Poly acrylic acid (PAA), Streptavidin, Bovine Serum Albumin, 2-Mercaptoethanol, MES hydrate were purchased from Sigma-Aldrich (St. Louis, MO). Biotin was supplied by TCI (Portland, OR), Sodium Phosphate Monobasic Monohydrate (7868) was purchased from Mallinckrodt (St. Louis, MO), Sodium Phosphate Dibasic anhydrous (SX0720-1), Green Fluorescent Protein (GFP) were purchased from EMD Millipore (Temecula, CA). p-STAT3 (Tyr 705) was supplied by Santa Cruz Biotechnology (Santa Cruz, CA), Recombinant Human STAT3 Protein, Anti-GFP Antibody conjugated with Biotin were purchased from abcam (Cambridge, MA), Biotin Mouse Anti-Mouse IgG2a [a] Clone 8.3 (RUO), Purified Mouse Anti-Stat3 (pY705) Clone 4/P-STAT3 (RUO) were purchased from BD Biosciences (San Jose, CA), Recombinant Human Epidermal Growth Factor (Gibco), Human IL-2 and IL-21 (Miltenyi biotec, Germany), EDC (1-ethyl-3-(3-dimethylaminopropyl)carbodiimide hydrochloride), NHS (N-hydroxysuccinimide), Antibiotic-Antimycotic, 100×, MEM Vitamin Solution, 100×, Ultra-Pure DNase/RNase-Free Distilled Water were obtained from Thermo Fisher Scientific (Rockford, IL). Minimum Essential Medium, Alpha 1×, L-Glutamine Solution, Fetal Bovine Serum, Trypsin EDTA were purchases from Mediatech, Inc. (Manassas, VA).

Optimization of Culture Conditions for Single Cell Assay

The human natural killer (NK) cell line NK-92 was purchased from American Type Culture Collection (ATCC #CRL-2407) (Manassas, VA) and were cultured according to American Type Culture Collection recommendation. Cells were maintained in α-MEM (GIBCO/BRL) supplemented with 12.5% horse serum (GIBCO, Carlsbad, CA), 12.5% FBS, 200 U/ml recombinant IL-2, 0.2 mM inositol, 0.1 mM β-mercaptoethanol, and 0.02 mM folic acid. Cells were never used above passage 10 and were cultured in a humidified incubator with 5% $CO_2$ at 37° C.

NK 92 cells were thawed to a seeding density of $4*10^6$ viable cells/mi. Initially, cells were grown in a suspension. The culture was fed adding small amounts of fresh medium every 2-3 days. Cell counts were performed to ensure cell density remained between 2*10⁶ and 4*10⁶ viable cells/mi. Human recombinant IL-2 was added to the media as the cells die quickly when IL-2 is depleted. NK-92 cells grow as non-adherent spheroid aggregates. To attach cells to the surface for single cell sensing, suspension culture was diluted and seeded in a 35 mm² petri dish which was coated aseptically with poly-L-lysine (1 ml/25 cm²). Briefly, poly-L-lysine was added to the plate and gently rocked to ensure even coating. After 5 mins, the solution was aspirated and washed with tissue culture grade water. The plates were dried for at least 2 hours before seeding the diluted cells. By this procedure, stable processing of cell image, sensing and repetitive stimulation of cell by exchanging medium became possible.

Fabrication of Protein Nanosensors

Nanosensors were fabricated from quartz capillaries with filaments, with outside diameter of 1.00 mm and inside diameter of 0.70 mm (Sutter Instrument Company, Novato, CA) using a P-2000 laser puller (Sutter Instrument Company, Novato, CA). The nanopipette surface was first modified with PLL, then with PAA, and then surface activated with EDC/NHS solution (10 mg/ml In MES buffer). This chemistry was used to bind streptavidin which was then used to bind the biotinylated antibodies, anti-npSTAT3 and anti-pSTAT3. The nanopipettes were backfilled with 10 mM phosphate buffer saline (PBS) solution at pH 7.4, centrifuged to remove residual air bubbles trapped at the tip of nanopipettes and kept in buffer until measurements were performed. An Ag/AgCl electrode was placed into the nanopipette as working electrode while another Ag/AgCl electrode was immersed in the cell media as a reference electrode. For calibration studies, anti-npSTAT3 and anti-pSTAT3 characterized nanosensors were used to measure concentration of npSTAT3 and pSTAT3 in solution at 30° C. Square wave voltammetry (SQV) was used for all measurements with a scan rate of 0.2 V s⁻¹ in the potential range of $-1000$ mV to 400 mV.

Calibration Studies and EGF and IL-21 Single Cell Stimulation Assays

For calibration studies, anti-npSTAT3 and anti-pSTAT3 antibodies (Abs) characterized nanosensor were used to measure concentration of npSTAT3 and pSTAT3 solution at 30° C. STAT3 and pSTAT3 calibration experiments were carried out at the following concentrations: 0.0083 ng/ml to 830 ng/ml with 10 fold dilutions. In between measurement, the sensor was dipped in a buffer solution to regenerate the nanopipette by effectively stripping it of any residually bound proteins (npSTAT3/pSTAT3). The control experiment was performed in buffer free solution of npSTAT3 and pSTAT3.

After calibration, single NK-92 cells were stimulated in the presence of EGF or IL-21 at 200 ng/ml concentration for various time periods (0, 5, 15, 20, 30 min). Measurements were taken after every 5 mins and each measurement lasted for approximately a minute. Levels of npSTAT3 and pSTAT3 detected were based on the calibration curves obtained from in-vitro measurements. Stimulated single cells were incubated in a humidified atmosphere at 37° C. with 5% $CO_2$.

Measurement of STAT3 and (p)-STAT3 Levels in Single NK-92 Cell

Based on our preliminary measurements, npSTAT3 and pSTAT3 levels in the cytoplasm and nucleus from stimulated vs non-stimulated single NK-92 cell were measured after 15 min of EGF stimulation and 10 min of IL-21 stimulation as determined by the stimulation assay. The intracellular protein sensing set-up consisted of an inverted microscope Olympus IX 70 with Spot Insight CMOS camera to image cells. The protein nanosensors were fixed to a microscope by a patch-clamp pipette holder (Axon Instruments) and the analytical characterization experiment was conducted as described before[5]. Square wave voltammetry (SQV) was utilized for all in vitro measurements with a scan rate of 0.1 V s⁻¹ in the potential range of $-1000$ mV to 400 mV. In-vivo measurements were done at a pre-determined fixed potential by combining the potentiostat and scanning ion conductance microscope (SICM) with a low-noise mechanical switch. The SICM setup consisted of an Axopatch 200B amplifier (Molecular Devices) for current feedback measurements, a MP-285 motorized micro-manipulator (Sutter Instrument Company, Novato, CA) for coarse positioning of multiplex nanosensor, a piezo stage (NanoCube, Physik Instrumente) for fine positioning and insertion of the protein nanosensor, and a programmable interface for hardware control of the setup. This system is run by custom software written in Lab-VIEW (National Instruments).

Flow Cytometry

For intracellular staining of NK-92 cells, cells were cocultured with cytokines at doses 20 ng/ml for IL-21 and 200 ng/ml for EGF for given timepoints. After stimulation, 5×10⁵ cells were mixed with 4% PFA at a 1:1 ratio to reach final 2%. Cells were incubated at 37° C. for 15 minutes, then taken into tubes for wash with PBS. Surface staining of cells were done with CD56 antibody (BD Biosciences, USA) for 20 minutes at 4° C. Surface antibody was washed and cells were permeabilized with 500 ul of 100% methanol and incubated for 20 minutes at 4° C. After two washes, cells were stained with STAT3-Y705 antibody (BD Biosciences, USA) for 30 minutes at 4° C. After two washes, cells were acquired at LSR Fortessa X-20 (BD Biosciences, USA) and sample analysis were completed using FlowJo Software (v10.4).

In Vivo Assays

Intracellular protein measurements were done in five replicates. Human rIL-21 and human EGF were used at a concentration of 200 ng/ml. All fluorescence microscopy analyses were carried out with a Leica SP5 confocal microscope using the Leica Application Suite Advance Fluorescence (LAS AF 3) software. Further image analyses were performed with Fiji-ImageJ software.

REFERENCES

1. Heath, J. R., Ribas, A. & Mischel, P. S. Single-cell analysis tools for drug discovery and development. *Nat. Rev. Drug Discov.* 15, 204-216 (2016).
2. Kang, C.-C. et al. Single cell-resolution western blotting. *Nat. Protoc.* 11, 1508-1530 (2016).
3. Sendra, V. G., Lie, A., Romain, G., Agarwal, S. K. & Varadarajan, N. Detection and isolation of auto-reactive human antibodies from primary B cells. *Methods San Diego Calif.* 64, (2013).
4. Bodenmiller, B. et al. Multiplexed mass cytometry profiling of cellular states perturbed by small-molecule regulators. *Nat. Biotechnol.* 30, 858-867 (2012).
5. Nascimento, R. A. S. et al. Single Cell "Glucose Nanosensor" Verifies Elevated Glucose Levels in Individual Cancer Cells. *Nano Lett.* 16, 1194-1200 (2016).
6. Actis, P. et al. Reversible thrombin detection by aptamer functionalized STING sensors. *Biosens. Bioelectron.* 26, 4503-4507 (2011).
7. Actis, P. et al. Compartmental Genomics in Living Cells Revealed by Single-Cell Nanobiopsy. *ACS Nano* 8, 546-553 (2014).

8. Actis, P. et al. *Copper Sensing with a Prion Protein Modified Nanopipette*. 2, (2012).
9. Actis, P., Mak, A. C. & Pourmand, N. Functionalized nanopipettes: toward label-free, single cell biosensors. *Bioanal. Rev.* 1, 177-185 (2010).
10. Özel, R. E., Lohith, A., Mak, W. H. & Pourmand, N. Single-cell intracellular nano-pH probes. *RSC Adv.* 5, 52436-52443 (2015).
11. Li, Q. et al. Multiple effects of IL-21 on human NK cells in ex vivo expansion. *Immunobiology* 220, 876-888 (2015).
12. Dien Bard, J. et al. IL-21 Contributes to JAK3/STAT3 Activation and Promotes Cell Growth in ALK-Positive Anaplastic Large Cell Lymphoma. *Am. J. Pathol.* 175, 825-834 (2009).
13. Zhu, M. et al. pSTAT3: a target biomarker to study the pharmacology of the anti-IL-21R antibody ATR-107 in human whole blood. *J. Transl. Med.* 11, 65 (2013).
14. Wan, C.-K. et al. Opposing roles of STAT1 and STAT3 in IL-21 function in CD4+ T cells. *Proc. Natl. Acad. Sci. U.S.A* 112, 9394-9399 (2015).
15. Wang, Y., van Boxel-Dezaire, A. H. H., Cheon, H., Yang, J. & Stark, G. R. STAT3 activation in response to IL-6 is prolonged by the binding of IL-6 receptor to EGF receptor. *Proc. Natl. Acad. Sci. U.S.A* 110, 16975-16980 (2013).
16. Han, W. & Lo, H.-W. Landscape of EGFR signaling network in human cancers: biology and therapeutic response in relation to receptor subcellular locations. *Cancer Lett.* 318, 124-134 (2012).
17. Boersema, P. J. et al. In-depth qualitative and quantitative profiling of tyrosine phosphorylation using a combination of phosphopeptide immunoaffinity purification and stable isotope dimethyl labeling. *Mol. Cell. Proteomics MCP* 9, 84-99 (2010).
18. Peck, S. C. Analysis of protein phosphorylation: methods and strategies for studying kinases and substrates. *Plant J. Cell Mol. Biol.* 45, 512-522 (2006).
19. Alizadeh, N., Hallaj, R. & Salimi, A. A highly sensitive electrochemical immunosensor for hepatitis B virus surface antigen detection based on Hemin/G-quadruplex horseradish peroxidase-mimicking DNAzyme-signal amplification. *Biosens. Bioelectron.* 94, 184-192 (2017).
20. Rébé C., Végran, F., Berger, H. & Ghiringhelli, F. STAT3 activation. *JAK-STAT* 2, (2013).
21. Croce, M., Rigo, V. & Ferrini, S. IL-21: A Pleiotropic Cytokine with Potential Applications in Oncology. *Journal of Immunology* Research (2015). doi:10.1155/2015/696578
22. Andl, C. D. et al. EGFR-induced cell migration is mediated predominantly by the JAK-STAT pathway in primary esophageal keratinocytes. *Am. J. Physiol.—Gastrointest. Liver Physiol.* 287, G1227-G1237 (2004).
23. Detection of Endogenous Pathway Activity in Novel Reporter Cell Lines. Sigma-Aldrich Available at: https://www.sigmaaldrich.com/technical-documents/articles/biowire/detection-of-endogenous-pathway-activity.html. (Accessed: 26 Nov. 2017)
24. Yahata, Y. et al. Nuclear Translocation of Phosphorylated STAT3 Is Essential for Vascular Endothelial Growth Factor-induced Human Dermal Microvascular Endothelial Cell Migration and Tube Formation. *J. Biol. Chem.* 278, 40026-40031 (2003).
25. Battaglia, A. et al. Interleukin-21 (IL-21) synergizes with IL-2 to enhance T-cell receptor-induced human T-cell proliferation and counteracts IL-2/transforming growth factor-β-induced regulatory T-cell development. *Immunology* 139, 109-120 (2013).

Notwithstanding the appended claims, the present disclosure is also defined by the following clauses:

1. A method for simultaneously detecting a first analyte and a second analyte in a biological sample, comprising:
    exposing a tip of a nanosensor to the biological sample, wherein the nanosensor defines an internal volume communicating with the biological sample via a nanoscale-sized opening of the tip, wherein the tip is functionalized with a first specific binding member for binding to the first analyte and a second specific binding member for binding to the second analyte, and wherein the nanosensor is part of a sensing apparatus comprising:
        a first electrode in contact with an electrolyte present within the internal volume of the nanosensor;
        a second electrode in contact with an electrolyte present on a side of the nanoscale-sized opening opposite the electrolyte present within the internal volume of the nanosensor;
        a circuit for controlling a voltage between the first and second electrodes; and
        a current detecting circuit adapted to measure ionic current flowing through the nanoscale-sized opening of the tip between the first electrode and the second electrode;
    applying a potential difference between the first electrode and the second electrode;
    measuring ionic current flow through the nanosensor tip to detect the first analyte and the second analyte in the biological sample; and
    distinguishing the first analyte from the second analyte based on a first diffusion limited current peak resulting from binding of the first specific binding member to the first analyte being distinguishable from a second diffusion limited current peak resulting from binding of the second specific binding member to the second analyte.

2. The method according to Clause 1, wherein the first analyte and the second analyte are independently selected from the group consisting of: a polymer, a protein, a nucleic acid, a polysaccharide, and a small molecule.

3. The method according to Clause 2, wherein the first analyte is a protein.

4. The method according to Clause 3, wherein the first specific binding member specifically binds a modified form of the protein.

5. The method according to Clause 4, wherein the modified form of the protein is a post-translational modification selected from the group consisting of: phosphorylation, glycosylation, ubiquitination, nitrosylation, methylation, acetylation, lipidation, and proteolysis.

6. The method according to Clause 4 or Clause 5, wherein the second specific binding member binds a corresponding protein lacking the modification.

7. The method according to Clause 6, wherein the second specific binding member specifically binds the corresponding protein lacking the modification.

8. The method according to Clause 2, wherein the first analyte is a nucleic acid.

9. The method according to Clause 8, wherein the nucleic acid is DNA or RNA.

10. The method according to any one of Clauses 1 to 9, wherein the biological sample is a single cell.

11. The method according to Clause 10, wherein the single cell is a prokaryotic cell or a eukaryotic cell.

12. The method according to Clause 10 or Clause 11, wherein the biological sample is a single living cell.

13. The method according to any one of Clauses 10 to 12, wherein exposing the tip of the nanosensor to the biological sample comprises inserting the tip into the cell.

14. The method according to Clause 13, wherein the tip is inserted into a pre-selected compartment of the cell.

15. The method according to Clause 14, wherein the pre-selected compartment is the cytoplasm.

16. The method according to Clause 15, wherein the pre-selected compartment is the cytosol or a cytoplasmic organelle.

17. The method according to Clause 14, wherein the pre-selected compartment is the nucleus.

18. The method according to any one of Clauses 1 to 9, wherein the biological sample is a cell lysate.

19. The method according to any one of Clauses 1 to 9, wherein the biological sample comprises proteins isolated from one or more cells.

20. The method according to any one of Clauses 1 to 9, wherein the biological sample comprises nucleic acids isolated from one or more cells.

21. The method according to any one of Clauses 1 to 20, wherein the first specific binding member and the second specific binding member are independently selected from the group consisting of: a polymer, a protein, a nucleic acid, an aptamer, and a chelating agent.

22. The method according to any one of Clauses 1 to 20, wherein at least one of the first specific binding member and the second specific binding member is a protein selected from the group consisting of: an antibody, a receptor, a ligand, a nucleic acid-binding protein, and an enzyme.

23. The method according to any one of Clauses 1 to 22, wherein applying a potential difference between the first electrode and the second electrode comprises applying a square wave potential between the first electrode and the second electrode.

24. The method according to Clause 23, wherein the square wave potential is in the range of −5000 mV to +5000 mV.

25. The method according to any one of Clauses 1 to 24, wherein the nanosensor is a nanopipette.

26. The method according to any one of Clauses 1 to 25, wherein the nanoscale-sized opening of the tip is from 10 to 200 nanometers.

27. A sensing apparatus, comprising:
   a nanosensor that comprises:
      a tip comprising a nanoscale-sized opening and functionalized with a first specific binding member for binding to a first analyte and a second specific binding member for binding to a second analyte; and
      an internal volume which, when in use, is in communication with a biological sample via the nanoscale-sized opening of the tip;
   a circuit for controlling a voltage between:
      a first electrode configured to contact an electrolyte present within the internal volume of the nanosensor, and
      a second electrode configured to contact an electrolyte present on a side of the nanoscale-sized opening opposite the electrolyte present within the internal volume of the nanosensor;
   a current detecting circuit configured to measure ionic current flowing through the nanoscale-sized opening of the tip between the first electrode and the second electrode; and
   a non-transitory computer-readable medium comprising instructions that, when in use, cause the sensing apparatus to:
      apply a potential difference between the first electrode and the second electrode;
      measure ionic current flow through the nanosensor tip to detect the first analyte and the second analyte in the biological sample; and
      distinguish the first analyte from the second analyte based on a first diffusion limited current peak resulting from binding of the first specific binding member to the first analyte being distinguishable from a second diffusion limited current peak resulting from binding of the second specific binding member to the second analyte.

28. The sensing apparatus of Clause 27, wherein the non-transitory computer-readable medium comprises instructions that, when in use, cause the sensing apparatus to apply a square wave potential between the first electrode and the second electrode.

29. The sensing apparatus of Clause 28, wherein the square wave potential is in the range of −5000 mV to +5000 mV.

30. The sensing apparatus of any one of Clauses 27 to 29, wherein the first specific binding member and the second specific binding member bind to an analyte independently selected from the group consisting of: a protein, a nucleic acid, a polysaccharide, and a small molecule.

31. The sensing apparatus of any one of Clauses 27 to 30, wherein the first specific binding member and the second specific binding member are independently selected from the group consisting of: a protein, a nucleic acid, an aptamer, and a chelating agent.

32. The sensing apparatus of any one of Clauses 27 to 31, wherein at least one of the first specific binding member and the second specific binding member is a protein selected from the group consisting of: an antibody, a receptor, a ligand, a nucleic acid-binding protein, and an enzyme.

33. The sensing apparatus of any one of Clauses 27 to 32, further comprising a controller attached to the nanosensor for effecting mechanical movement of the nanosensor in one or more of the x, y, and z directions.

34. The sensing apparatus of any one of Clauses 27 to 33, comprising a scanning ion conductance microscope (SICM).

35. The sensing apparatus of Clause 34, wherein the non-transitory computer-readable medium comprises instructions that, when in use, cause the SICM of the sensing apparatus to image the topography of a biological sample or component thereof and allow positioning of the nanosensor tip at a desired location of the biological sample.

36. The sensing apparatus of any one of Clauses 27 to 35, wherein the nanosensor is a nanopipette.

37. The sensing apparatus of any one of Clauses 27 to 36, wherein the nanoscale-sized opening of the tip is from 10 to 200 nanometers.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method for simultaneously detecting a first analyte and a second analyte in a biological sample, comprising:
exposing a tip of a nanosensor to the biological sample, wherein the nanosensor defines an internal volume communicating with the biological sample via a nanoscale-sized opening of the tip, wherein the tip is functionalized with a first specific binding member for binding to the first analyte and a second specific binding member for binding to the second analyte, and wherein the nanosensor is part of a sensing apparatus comprising:
  a first electrode in contact with an electrolyte present within the internal volume of the nanosensor;
  a second electrode in contact with an electrolyte present on a side of the nanoscale-sized opening opposite the electrolyte present within the internal volume of the nanosensor;
  a circuit for controlling a voltage between the first and second electrodes; and
  a current detecting circuit adapted to measure ionic current flowing through the nanoscale-sized opening of the tip between the first electrode and the second electrode;
applying a square wave potential between the first electrode and the second electrode;
measuring ionic current flow through the nanosensor tip to detect the first analyte and the second analyte in the biological sample; and
distinguishing the first analyte from the second analyte based on a first diffusion limited current peak resulting from binding of the first specific binding member to the first analyte being distinguishable from a second diffusion limited current peak resulting from binding of the second specific binding member to the second analyte.

2. The method according to claim 1, wherein the first analyte and the second analyte are independently selected from the group consisting of: a polymer, a protein, a nucleic acid, a polysaccharide, and a small molecule.

3. The method according to claim 2, wherein the first analyte is a protein.

4. The method according to claim 3, wherein the first specific binding member specifically binds a modified form of the protein.

5. The method according to claim 4, wherein the modified form of the protein is a post-translational modification selected from the group consisting of: phosphorylation, glycosylation, ubiquitination, nitrosylation, methylation, acetylation, lipidation, and proteolysis.

6. The method according to claim 3, wherein the second specific binding member binds a corresponding protein lacking the modification, optionally wherein the second specific binding member specifically binds the corresponding protein lacking the modification.

7. The method according to claim 2, wherein the first analyte is DNA or RNA.

8. The method according to claim 1, wherein the biological sample is a single cell, optionally wherein the single cell is a single living cell.

9. The method according to claim 8, wherein the single cell is a prokaryotic cell or a eukaryotic cell.

10. The method according to claim 8, wherein exposing the tip of the nanosensor to the biological sample comprises inserting the tip into the cell.

11. The method according to claim 10, wherein the tip is inserted into a pre-selected compartment of the cell selected from the cytosol, a cytoplasmic organelle, or the nucleus.

12. The method according to claim 1, wherein the first specific binding member and the second specific binding member are independently selected from the group consisting of: a polymer, a protein, an antibody, a receptor, a ligand, a nucleic acid-binding protein, an enzyme, a nucleic acid, an aptamer, and a chelating agent.

13. The method according to claim 1, wherein the square wave potential is in the range of −5000 mV to +5000 mV.

14. The method according to claim 1, wherein the nanosensor is a nanopipette.

15. The method according to claim 1, wherein the nanoscale-sized opening of the tip is from 10 to 200 nanometers.

* * * * *